(12) United States Patent
Zaliha et al.

(10) Patent No.: US 8,623,996 B2
(45) Date of Patent: Jan. 7, 2014

(54) COLD ACTIVE ENZYME AND METHOD THEREOF

(75) Inventors: Raja Noor Zaliha, Selangor (MY); Abu Bakar Salleh, Selangor (MY); Mahiran Basri, Selangor (MY); Mohd Shukuri Bin Mohamad Ali, Selangor (MY)

(73) Assignee: University Putra Malaysia, Serdang Baharu (MY)

( * ) Notice: Subject to any disclaimer, the term of this patent is extended or adjusted under 35 U.S.C. 154(b) by 376 days.

(21) Appl. No.: 12/877,714

(22) Filed: Sep. 8, 2010

(65) Prior Publication Data
US 2012/0058514 A1 Mar. 8, 2012

(51) Int. Cl.
*C07K 1/00* (2006.01)

(52) U.S. Cl.
USPC ............... 530/350; 530/300; 435/71; 435/7.1

(58) Field of Classification Search
None
See application file for complete search history.

(56) References Cited

U.S. PATENT DOCUMENTS 7,517,684 B2 * 4/2009 Rubenfield et al. ........... 435/325

OTHER PUBLICATIONS

Wells, Biochemistry, vol. 29, pp. 8509-8517, 1990.*

* cited by examiner

*Primary Examiner* — Hope Robinson
(74) *Attorney, Agent, or Firm* — Edwards Wildman Palmer LLP; Ralph A. Loren; Richard B. Emmons

(57) ABSTRACT

The objective of the present invention is to obtain a low temperature producing enzyme and more particularly, the enzyme provides a bifunctional purpose of varying its enzyme activity into activity of another enzyme. The present invention has overcome problems such as ability of obtaining an enzyme at low temperature.

7 Claims, 29 Drawing Sheets

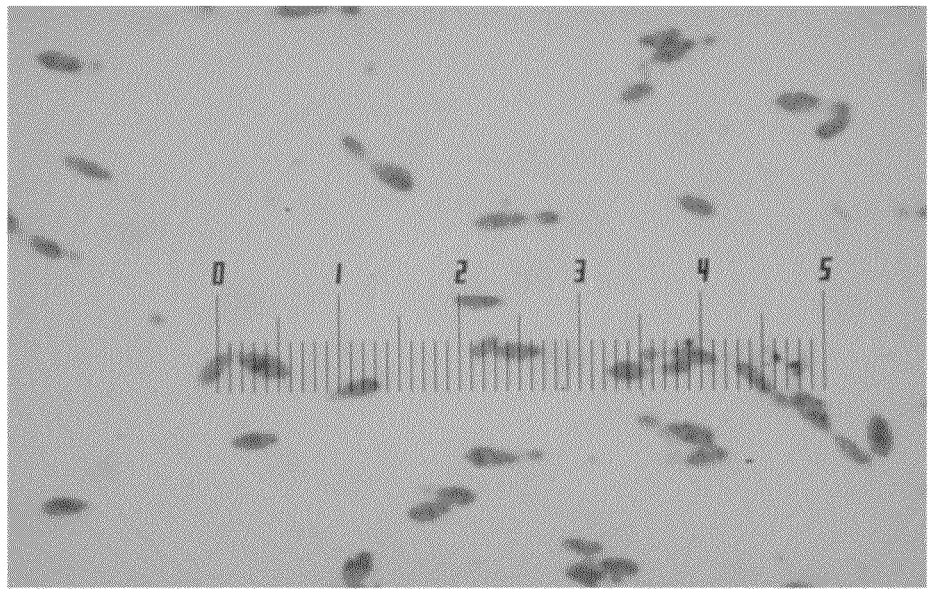
Figure 1: Microscopic structure of the microorganism PI 12.
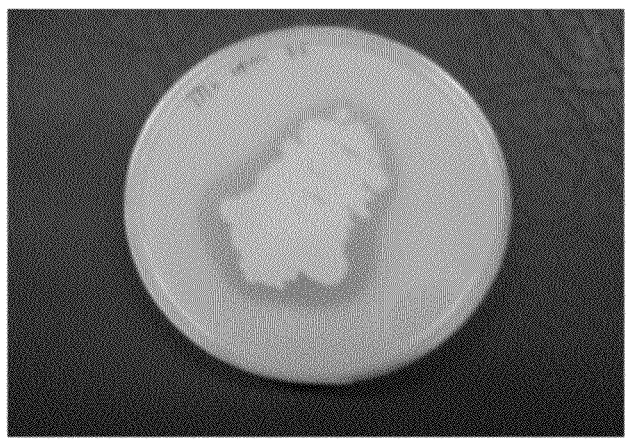
Figure 2: Clear halo formed on tributyrin agar plates.

Figure 5: Genomic DNA of islolate PI 12 electrophoresed on 1% agarose gel

Figure 6: PCR product electroeluted on 1% agarose.

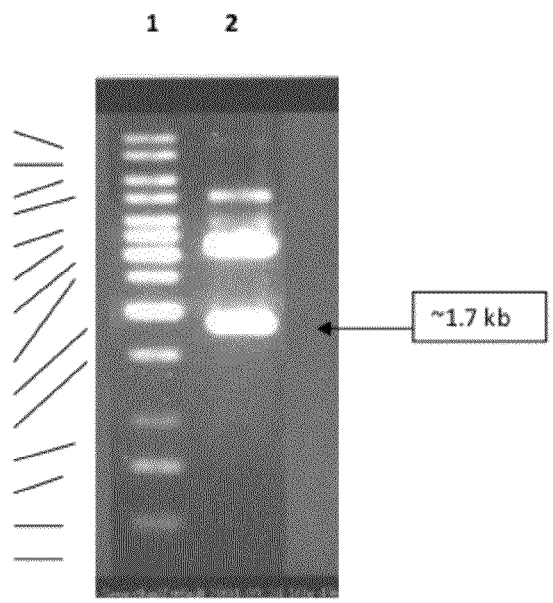
Figure 10: The fragment of the suspected lipase gene (~1.7 kb) electroeluted on 1% agarose. Lane 1: 1 kb DNA marker; Lane 2: Digested pRSET (2.9 kb) with insert.

```
tatgtcagcgatatctactcgctgggcaagttcagcgccttttccgcgcagcagcaggcc
 Y  V  S  D  I  Y  S  L  G  K  F  S  A  F  S  A  Q  Q  Q  A
caggccaagtcgtcgctgcaatcctggtcggacgtcaccaatatccacttcgtcgacgcc
 Q  A  K  S  S  L  Q  S  W  S  D  V  T  N  I  H  F  V  D  A
ggccagggcgatcagggcgacctgaccttcggcaacttcagcagtagtgtcggcggtgcg
 G  Q  G  D  Q  G  D  L  T  F  G  N  F  S  S  S  V  G  G  A
gcgttcgccttcctgccggatgtaccggatgcgctcaagggcaatcctggtacctgatc
 A  F  A  F  L  P  D  V  P  D  A  L  K  G  Q  S  W  Y  L  I
aacagcagctacagcgccaacgtcaatccggccaacggcaactacggacgccagaccctg
 N  S  S  Y  S  A  N  V  N  P  A  N  G  N  Y  G  R  Q  T  L
acccacgagatcggccataccctgggcctgagccaccccggcgactacaacgccggcgag
 T  H  E  I  G  H  T  L  G  L  S  H  P  G  D  Y  N  A  G  E
ggcgatcccacctacgccgacgctacctacgccgaggacacccgcgcctattcggtgatg
 G  D  P  T  Y  A  D  A  T  Y  A  E  D  T  R  A  Y  S  V  M
agctactgggaagagcagaacaccggccaggacttcaagggcgcctattcctcggcaccg
 S  Y  W  E  E  Q  N  T  G  Q  D  F  K  G  A  Y  S  S  A  P
ctgctggacgacatcgcggcgatccagaagctctacggggccaacctgaccacccgcacc
 L  L  D  D  I  A  A  I  Q  K  L  Y  G  A  N  L  T  T  R  T
ggcgacacggtgtacggcttcaactccaacaccgagcgcgacttctacagcgccacctcg
 G  D  T  V  Y  G  F  N  S  N  T  E  R  D  F  Y  S  A  T  S
tccagttccaagctggtgttctcggtgtgggacgccggcggcaacgacaccctggacttc
 S  S  S  K  L  V  F  S  V  W  D  A  G  G  N  D  T  L  D  F
Tccggcttcagccagaaccagaagatcaacctcaacgagaaggcgctgtccgatgtcggc
 S  G  F  S  Q  N  Q  K  I  N  L  N  E  K  A  L  S  D  V  G
gggttgaagggcaatgtgtcgatcgctgccggggtcaccgtggaaaacgccatcggcggc
 G  L  K  G  N  V  S  I  A  A  G  V  T  V  E  N  A  I  G  G
tcgggtagcgacctgttgatcggcaacgacgtggccaacgtgctcaagggcggcgccggc
 S  G  S  D  L  L  I  G  N  D  V  A  N  V  L  K  G  G  A  G
aacgacatcctctacggcggcctcggcgcggaccagctgtggggtggcgcgggagccgac
 N  D  I  L  Y  G  G  L  G  A  D  Q  L  W  G  G  A  G  A  D
accttcgtctacggcgatatcgccgagtcctccgcggcggcgccggataccctgcgcgac
 T  F  V  Y  G  D  I  A  E  S  S  A  A  A  P  D  T  L  R  D
ttcgtcagcggccaggacaagatcgacctgtccgggctggacgccttcgtcaacggcggg
 F  V  S  G  Q  D  K  I  D  L  S  G  L  D  A  F  V  N  G  G
ctggtgctgcaatacgtcgacgccttcgccggcaaggccggccaggcgatcctgtcctac
 L  V  L  Q  Y  V  D  A  F  A  G  K  A  G  Q  A  I  L  S  Y
gacgcggcgagcaaggccggcagcctggcgatcgacttcagcggggacgcccatgccgat
 D  A  A  S  K  A  G  S  L  A  I  D  F  S  G  D  A  H  A  D
ttcgcgatcaatctgatcggccaggcgacccaggccgacatcgtcgtcagaagcgattga
 F  A  I  N  L  I  G  Q  A  T  Q  A  D  I  V  V  R  S  D  -
ggatatcacgtgggatcc
 G  Y  H  V  G  S
```

Figure 11: Nucleotide sequence and its deduced amino acids of LipPI12 comprising 780 nucleotides and 260 amino acids, respectively.

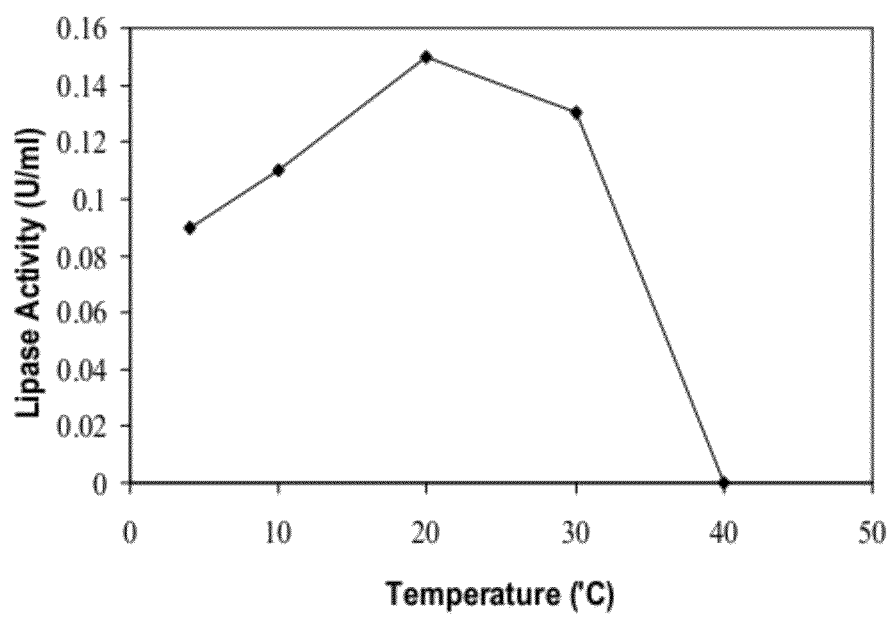
Figure 12: Effect of crude lipase activity at different temperatures.

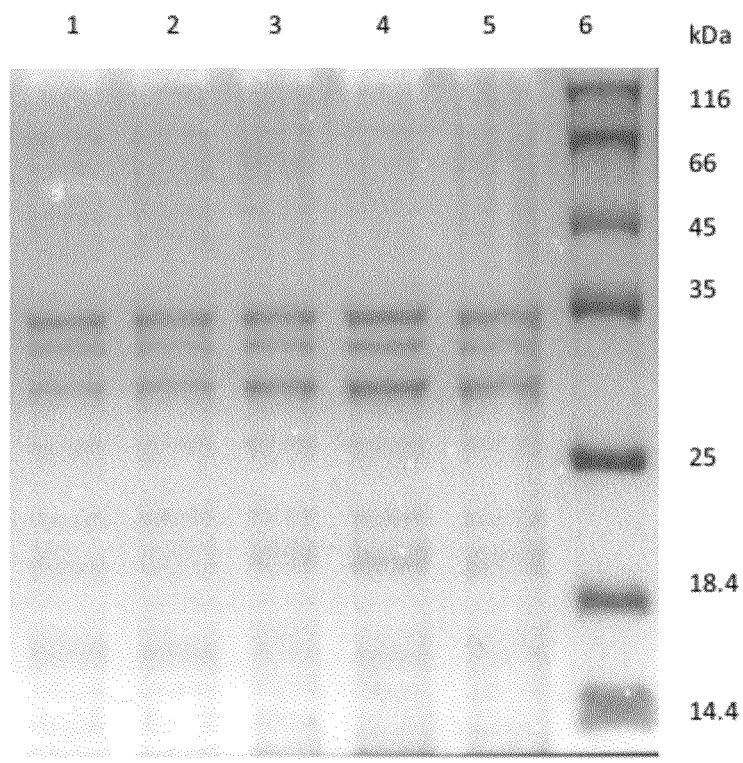
Figure 13: Expression profile of cold adapted lipase at different concentrations of IPTG.

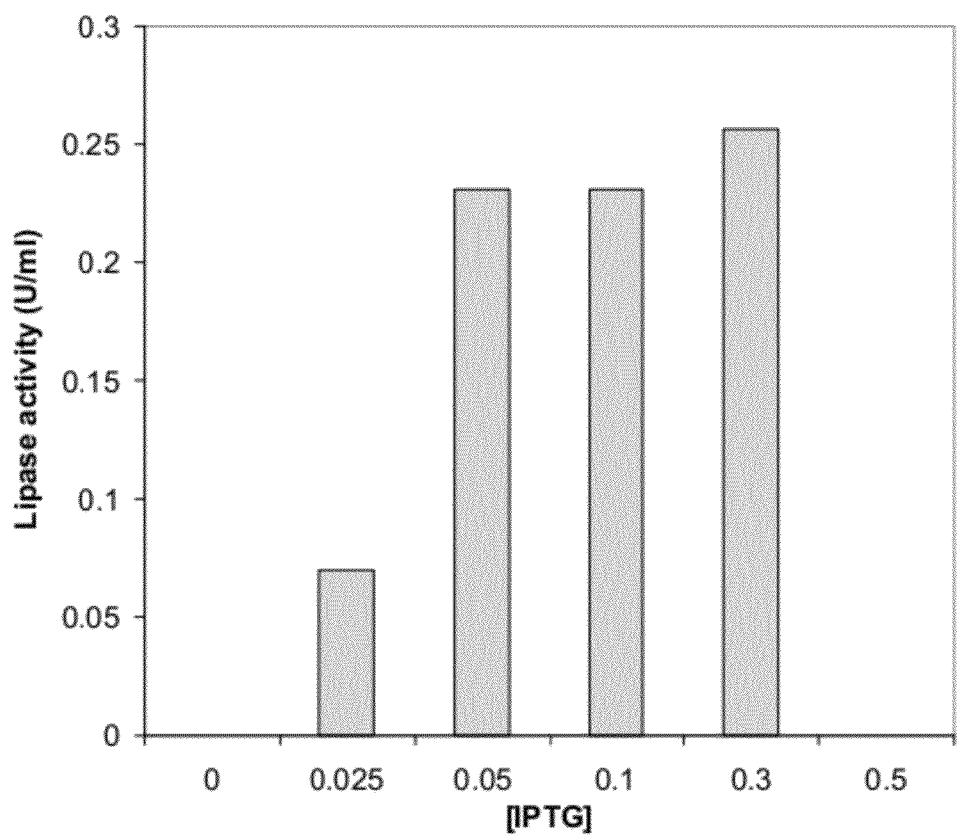
Figure 14: The optimum concentration of IPTG for the intracellular expression of cold adapted lipase gene in *E.coli*.

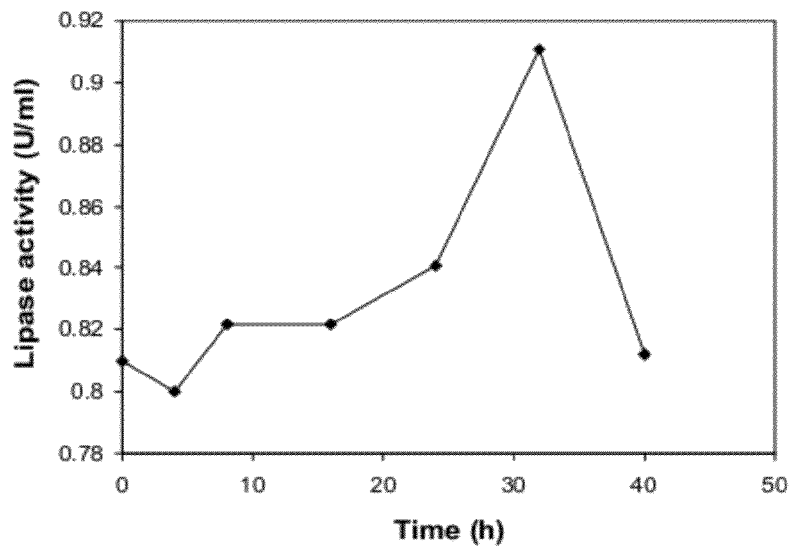
Figure 15: The effect of lipase expression at different time interval.
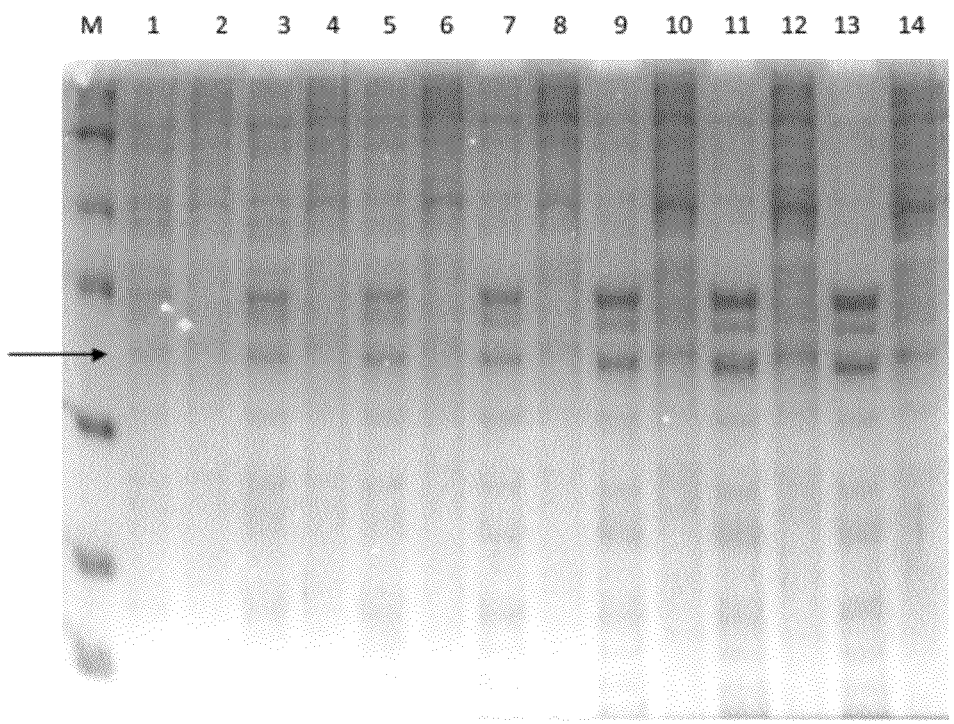
Figure 16: Soluble and insoluble fractions of the recombinant lipase (indicated by the arrows).

Figure 17: Optimization of IPTG concentration on secretory expression of recombinant cold adapted lipase.
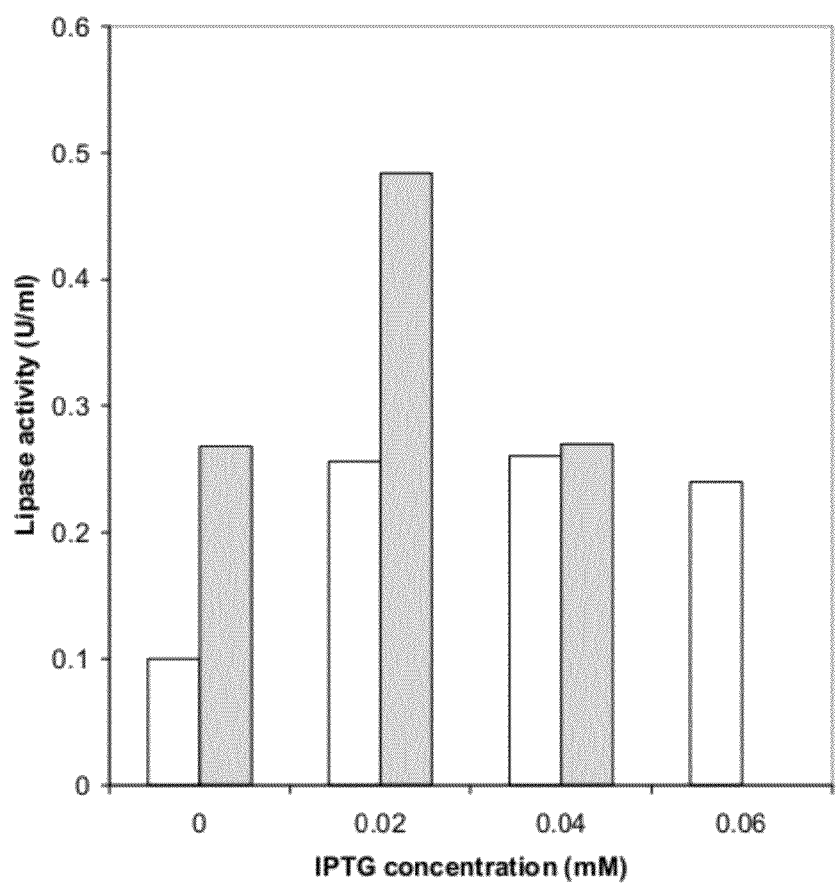

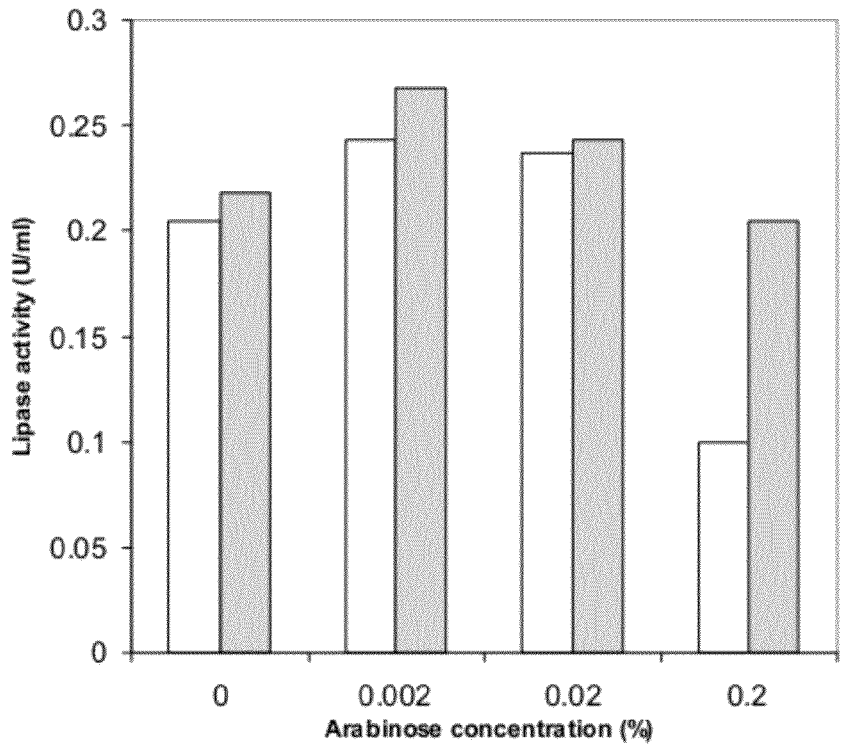
Figure 18: The effect of intracellular and extracellular expressions at different L-arabinose concentrations.
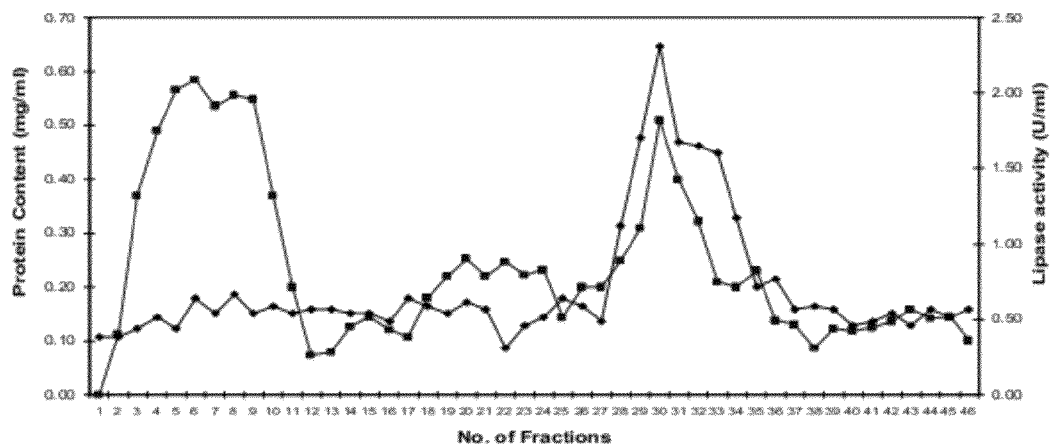
Figure 19: Purification profile of the recombinant intracellularly expressed LipPI12 from affinity chromatography.

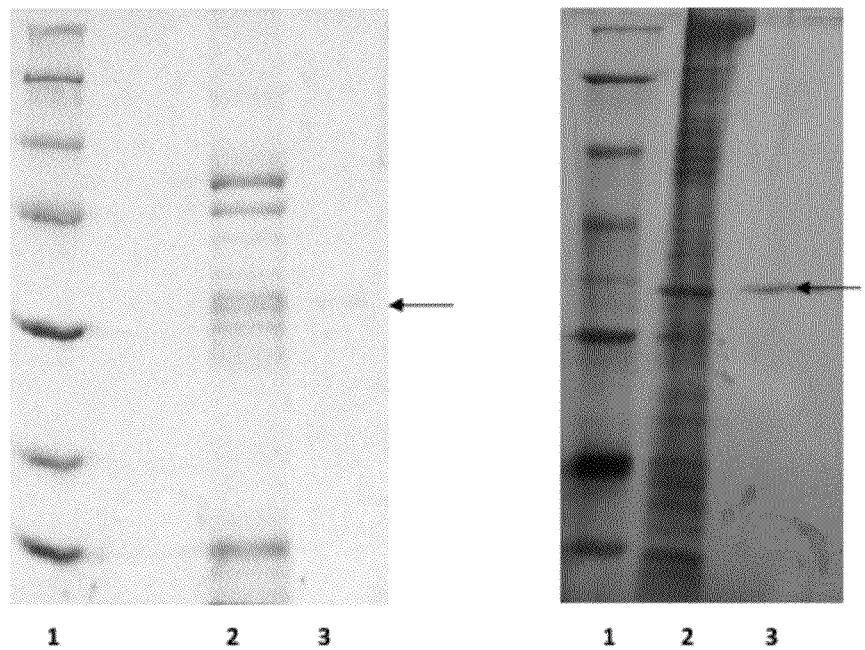
Figure 20: The SDS PAGE (A) and native PAGE (B) of the purified recombinant intracellularly expressed cold adapted LipPI12.
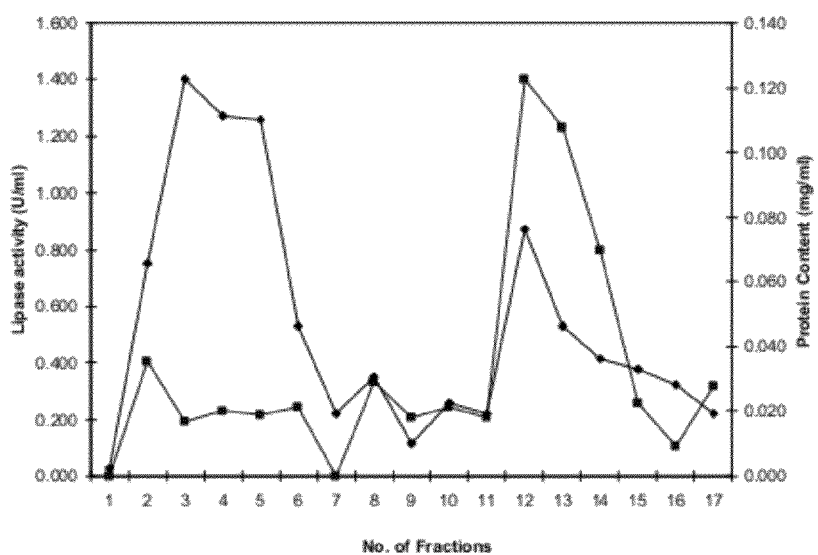
Figure 21: Purification profile of the recombinant extracellularly expressed cold adapted LipPI12 from affinity chromatography.

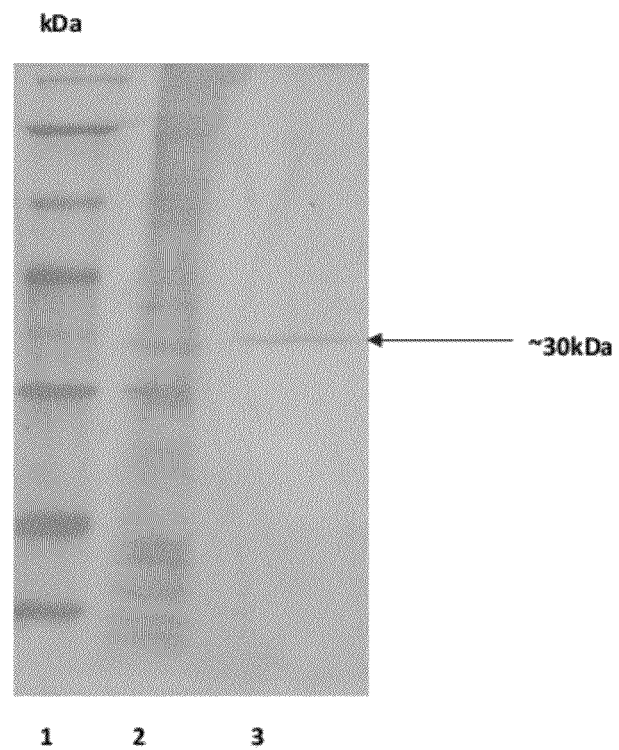
Figure 22: Purified extracellularly expressed recombinant cold adapted LipPI12 electroeluted using SDS PAGE (stained via silver staining method).
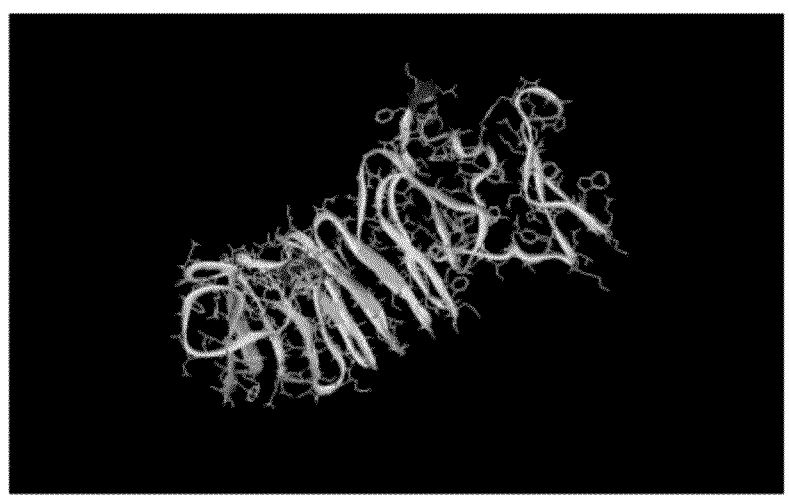
Figure 23: Predicted model of the cold adapted lipase from *Leucosporodium antarcticum* sp. strain PI12

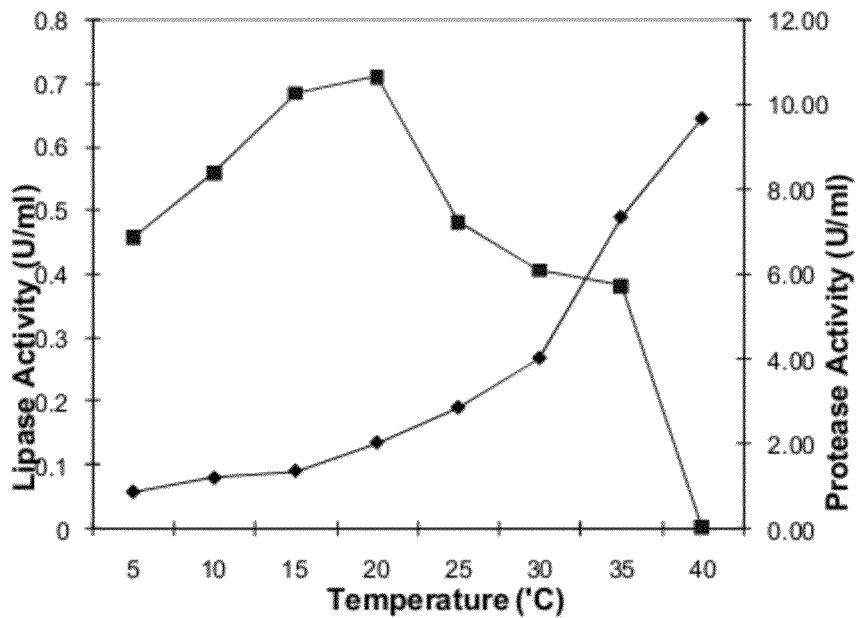
Figure 24: Optimum temperature profile of LipPI12 lipase and protease.
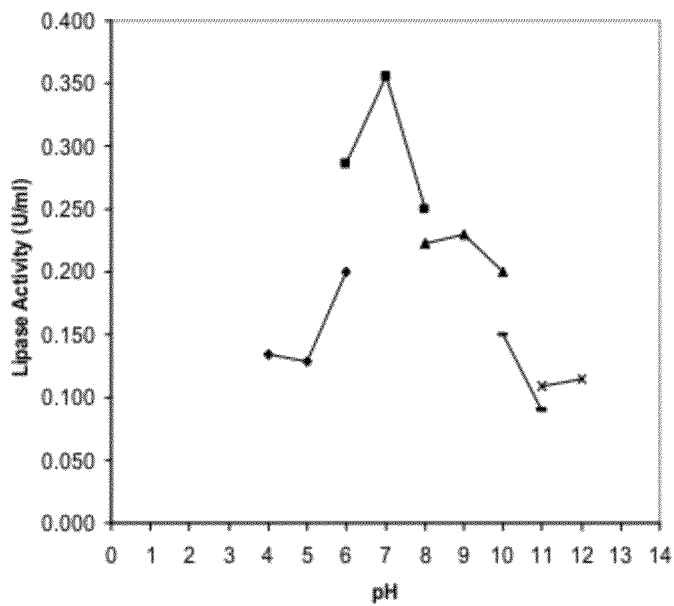
Figure 25: pH profile of LipPI12 lipase.

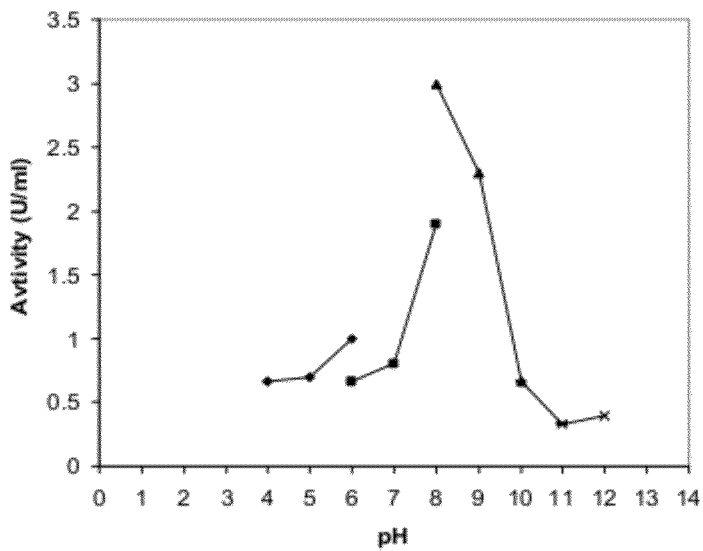
Figure 26: pH profile of LipPI12 protease.
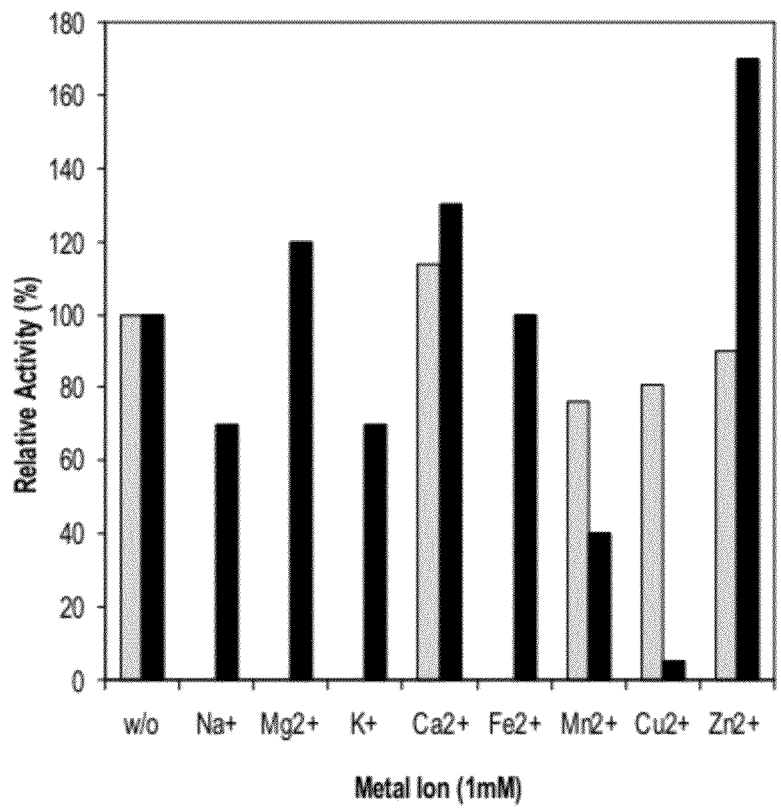
Figure 27: Effect of metal ions on LipPI12 lipase and protease activities.

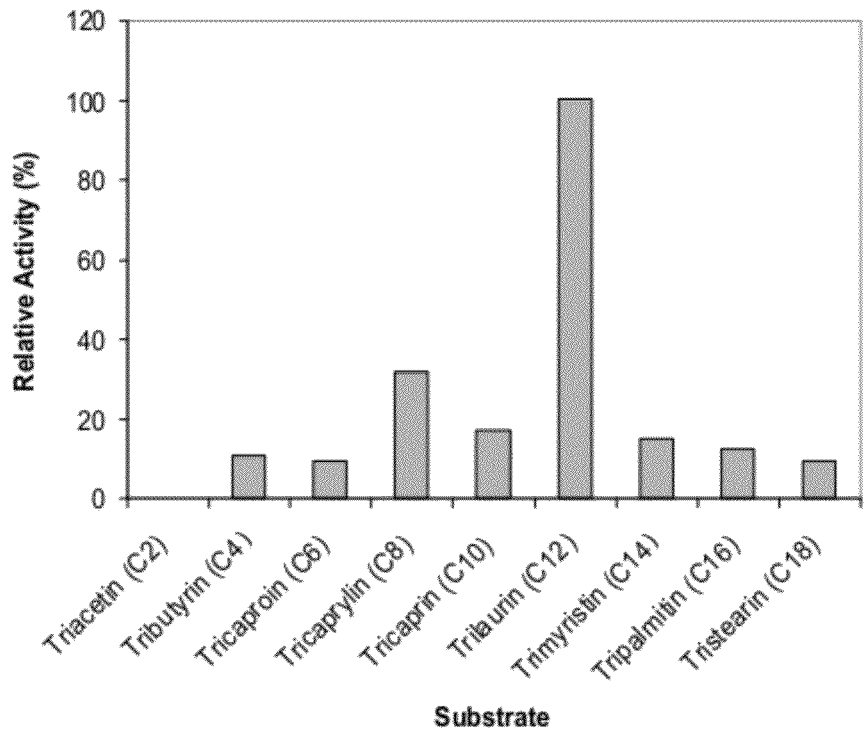
Figure 28: Effect of pure triglycerides on LipPI12 lipase activity.
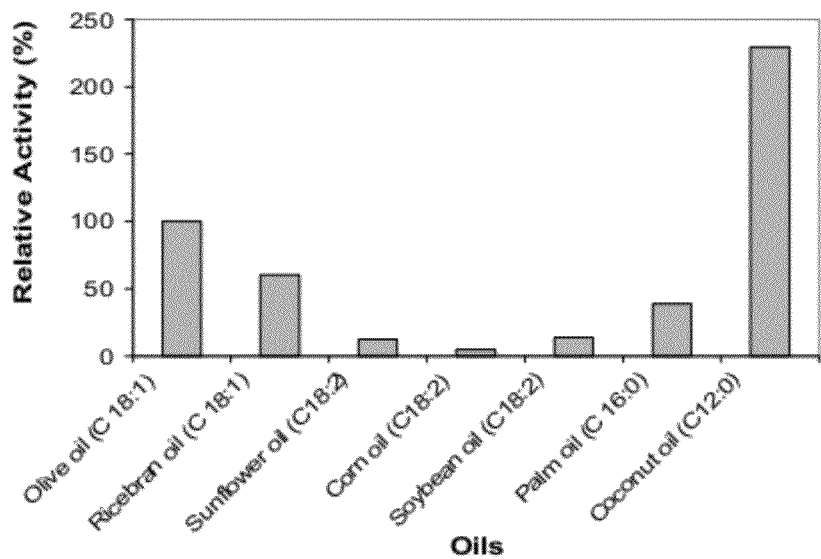
Figure 29: Effect of various natural oils on LipPI12 lipase activity.

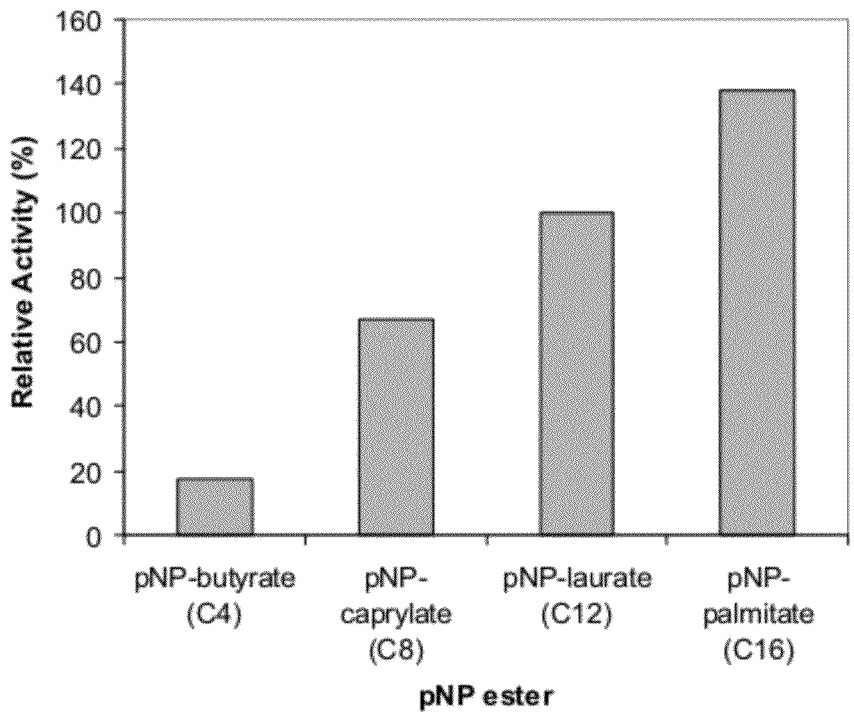
Figure 30: LipPl12 hydrolysis profile on para-nitrophenyl esters.
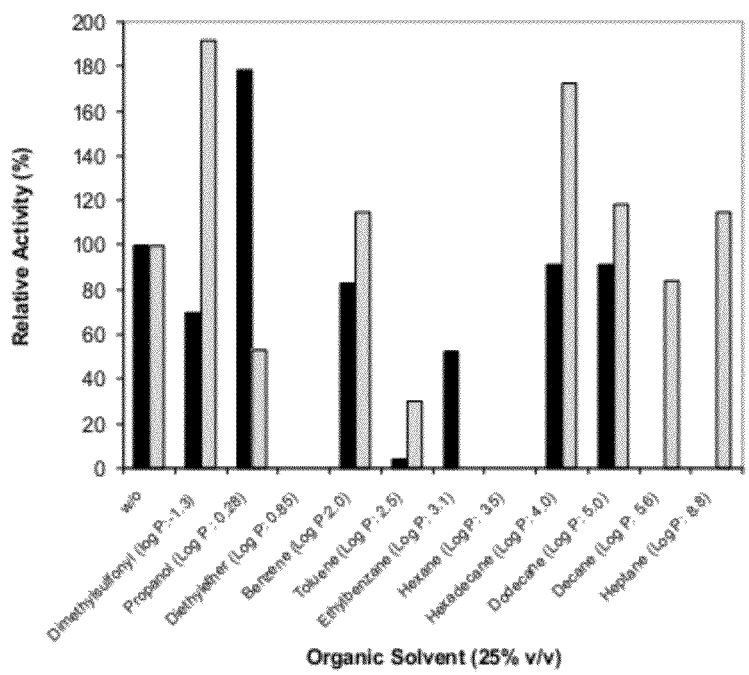
Figure 31: Effect of various organic solvents on LipPl12 activity.

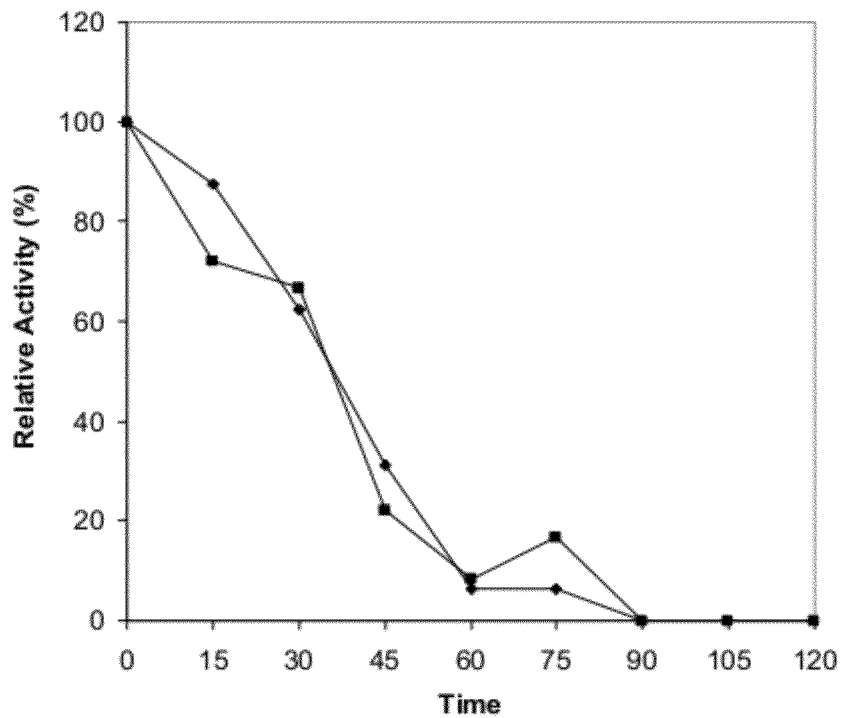
Figure 32: Thermostability profile of LipPI12 lipase.
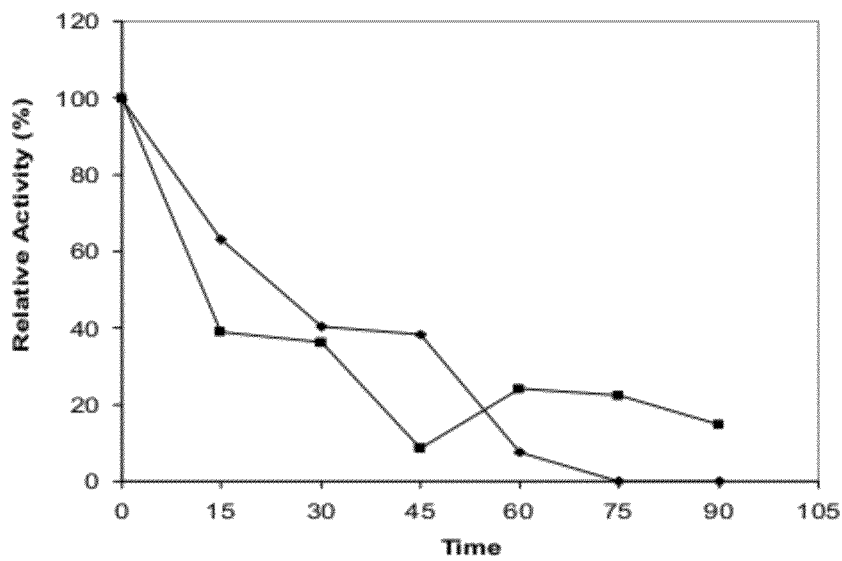
Figure 33: Thermostability profile of LipPI12 protease.

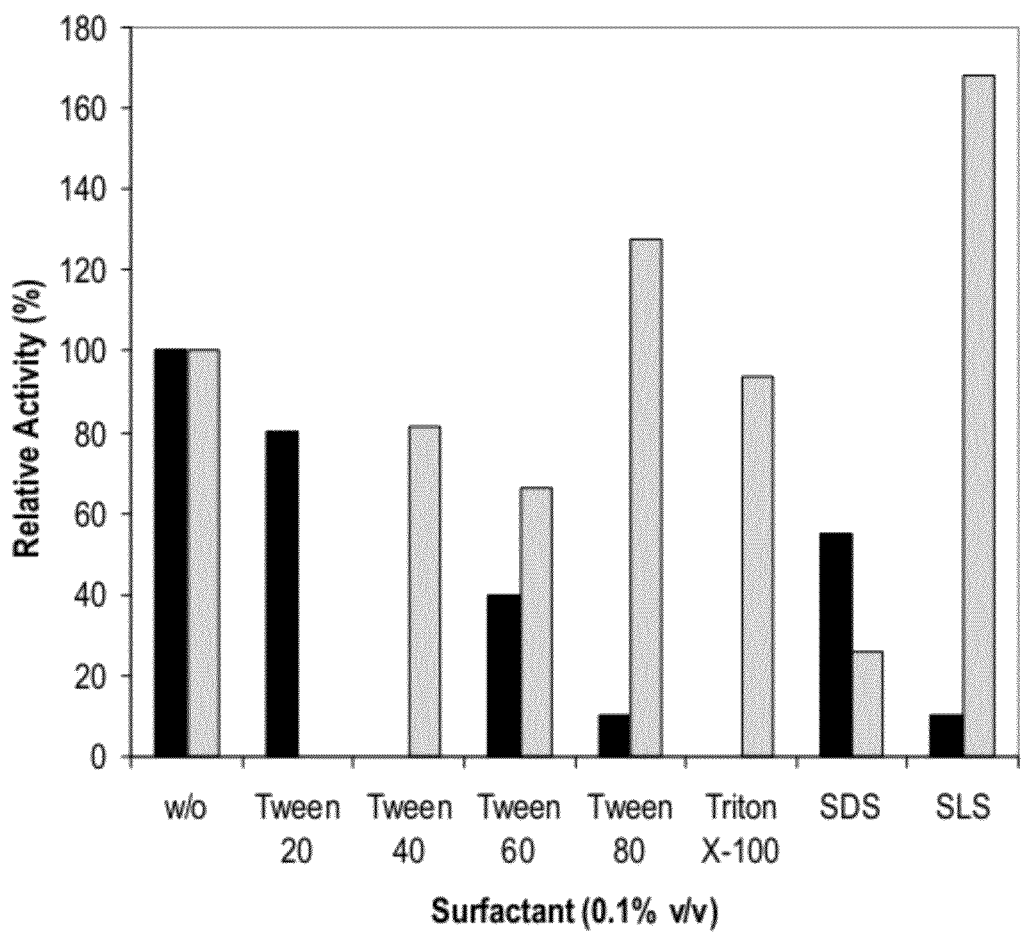
Figure 34: Effect of various surfactants on both LipPI12 lipase and protease activities.

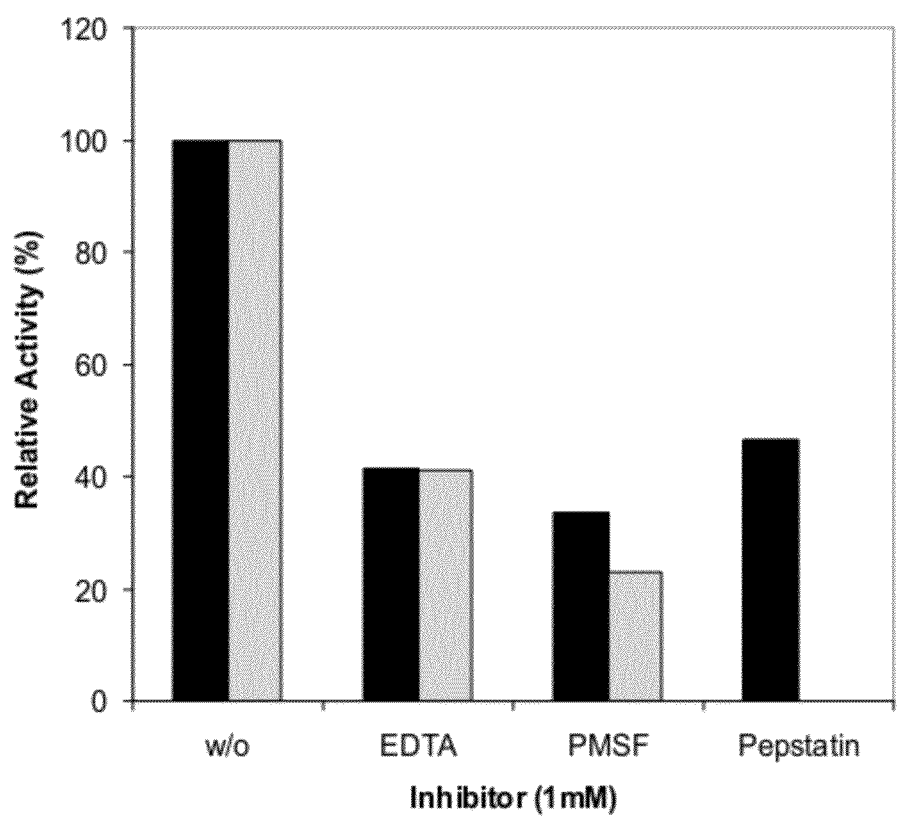
Figure 35: Effect of inhibitors on LipPI12 lipase and protease activities.

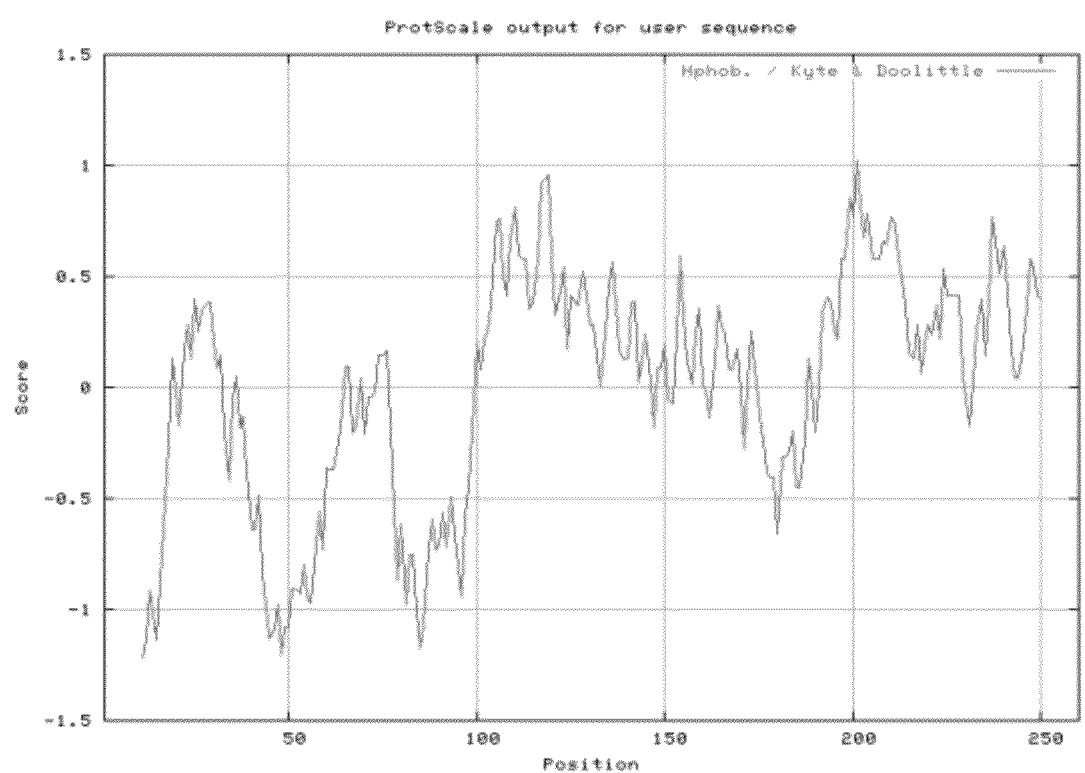
Figure 36: Hydrophobicity profile of LipPI12.

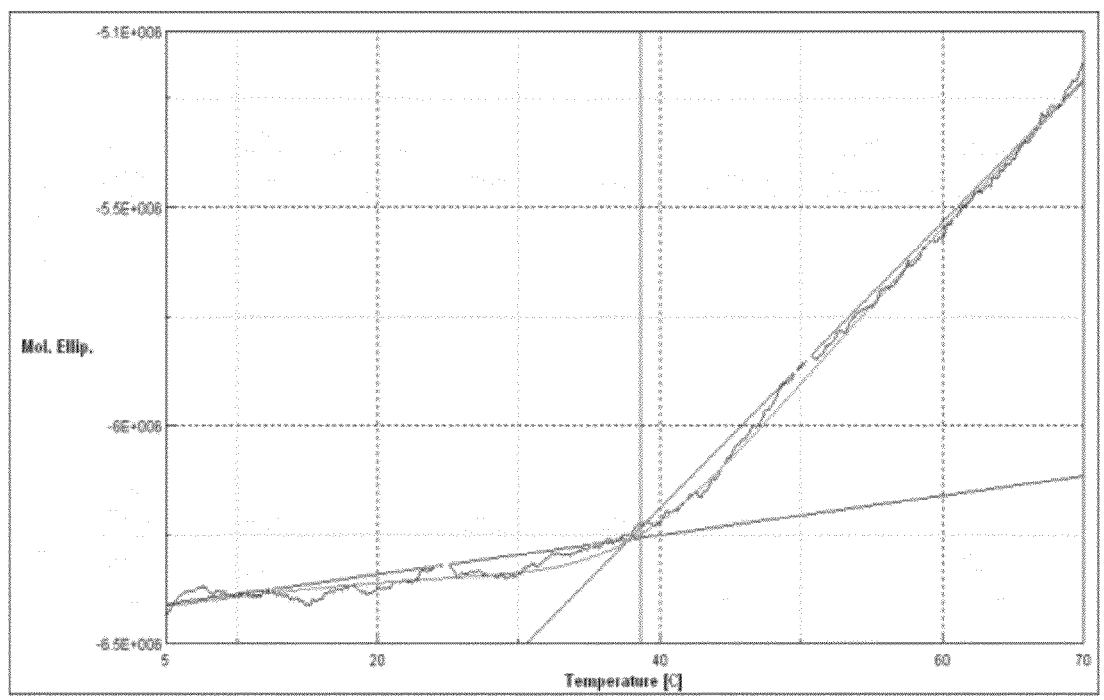
Figure 37: Melting point (T$_m$) determination of LipPI12, ranging from 5 - 70°C.

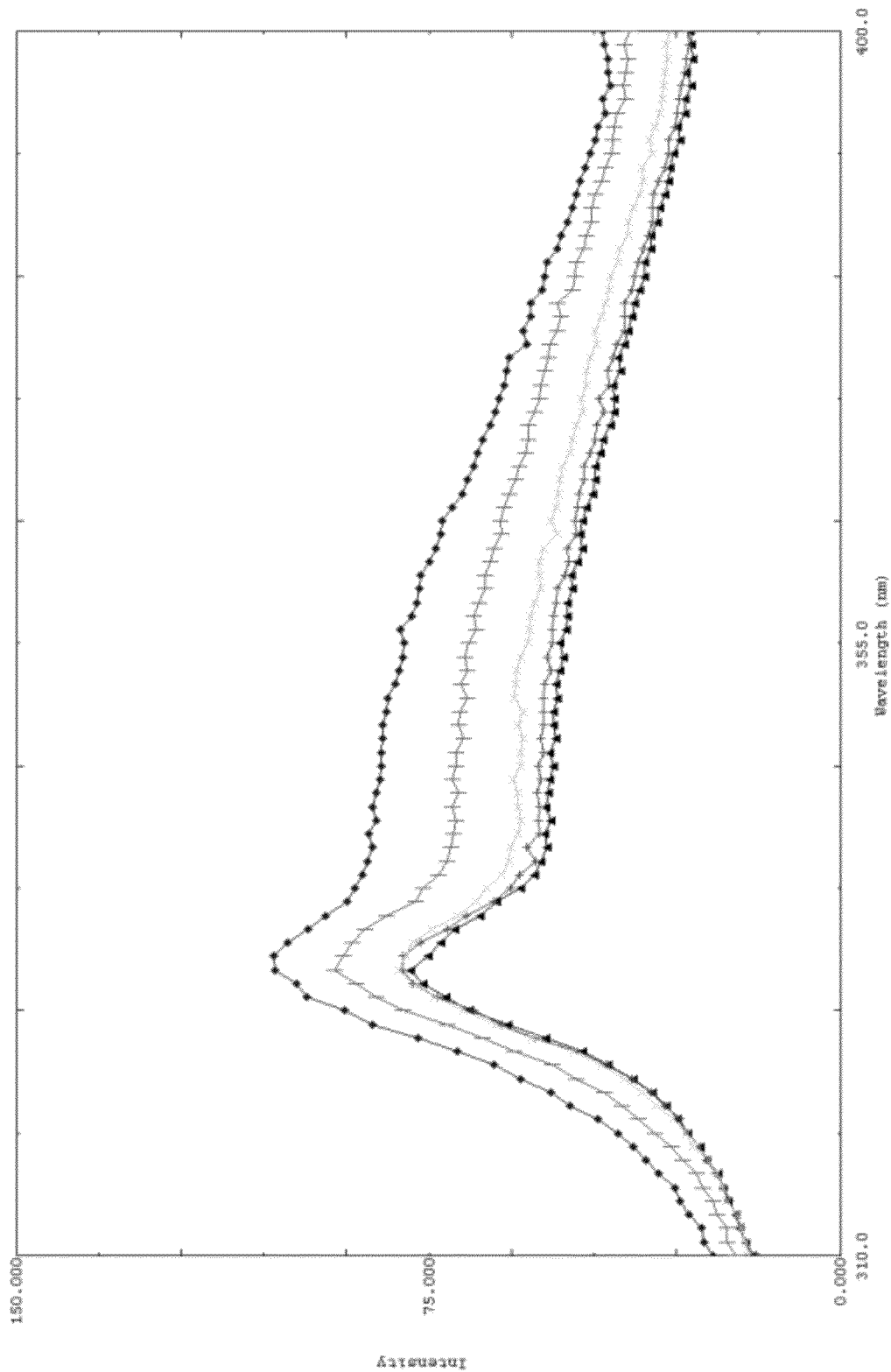
Figure 38 : Intrinsic value of LipPl12 fluorescence emission at various temperatures.

Figure 39: Location of Trp (W) residue in LipPI12, shown from the predicted model

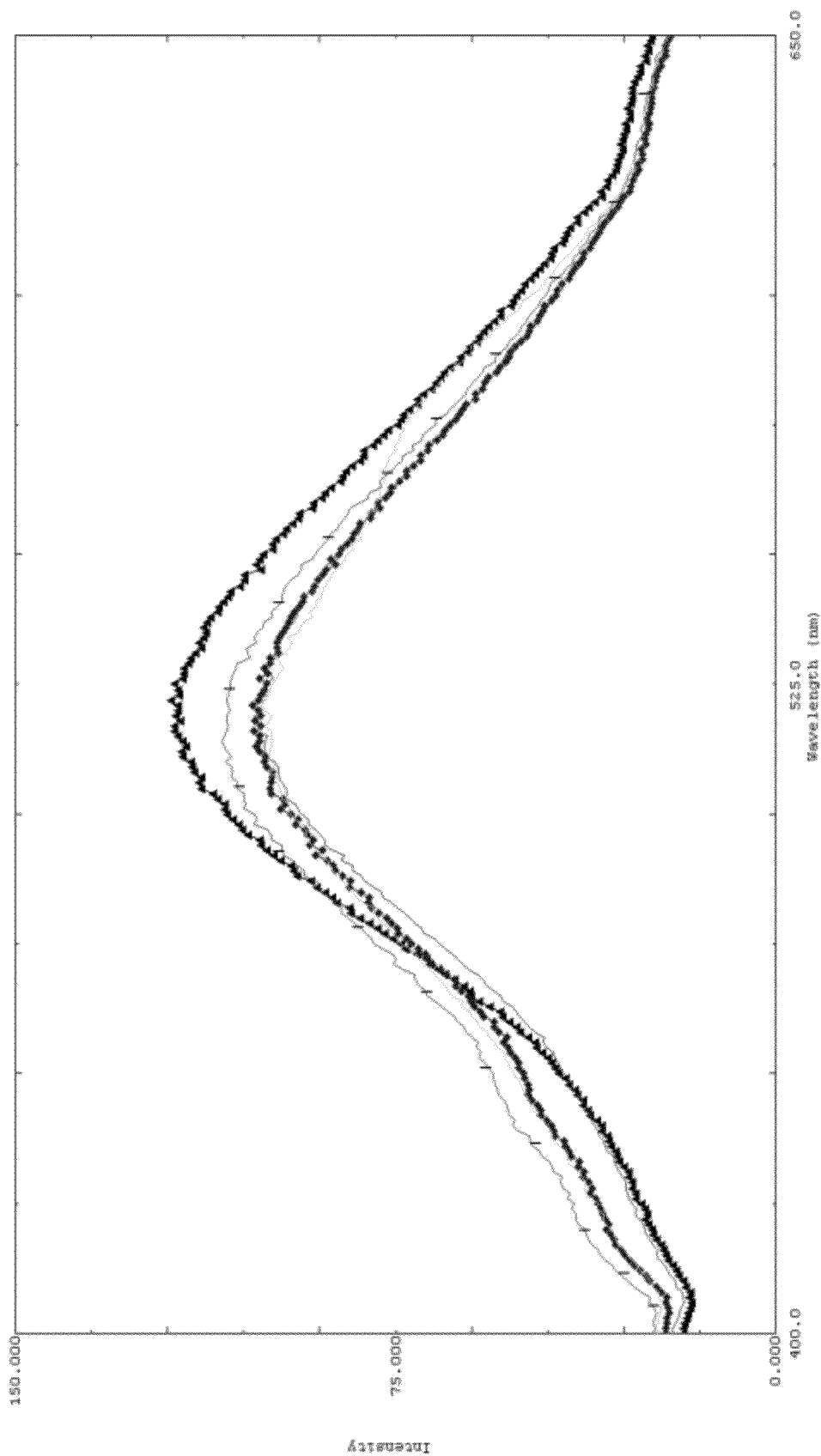
Figure 40: Intrinsic value of the LipPI12 fluorescence emission at various temperatures

Figure 41: Hydrophobic residues in LipPI12

SEQUENCE LISTING

<160> NUMBER OF SEQ ID NOS: 5

<210> SEQ ID NO 1
<211> LENGTH: 1218
<212> TYPE: DNA
<213> ORGANISM: Leucosporidium antarcticum
<220> FEATURE:
<221> NAME/KEY: CDS
<222> LOCATION: (1)..(1197)

<400> SEQUENCE: 1 tat gtc agc gat atc tac tcg ctg ggc aag ttc agc gcc ttt tcc gcg        48

```
Tyr Val Ser Asp Ile Tyr Ser Leu Gly Lys Phe Ser Ala Phe Ser Ala
 1               5                  10                  15 cag cag cag gcc cag gcc aag tcg tcg ctg caa tcc tgg tcg gac gtc         96
Gln Gln Gln Ala Gln Ala Lys Ser Ser Leu Gln Ser Trp Ser Asp Val
                 20                  25                  30 acc aat atc cac ttc gtc gac gcc ggc cag ggc gat cag ggc gac ctg        144
Thr Asn Ile His Phe Val Asp Ala Gly Gln Gly Asp Gln Gly Asp Leu
             35                  40                  45 acc ttc ggc aac ttc agc agt agt gtc ggc ggt gcg gcg ttc gcc ttc        192
Thr Phe Gly Asn Phe Ser Ser Ser Val Gly Gly Ala Ala Phe Ala Phe
         50                  55                  60 ctg ccg gat gta ccg gat gcg ctc aag ggg caa tcc tgg tac ctg atc        240
Leu Pro Asp Val Pro Asp Ala Leu Lys Gly Gln Ser Trp Tyr Leu Ile
 65              70                  75                  80 aac agc agc tac agc gcc aac gtc aat ccg gcc aac ggc aac tac gga        288
Asn Ser Ser Tyr Ser Ala Asn Val Asn Pro Ala Asn Gly Asn Tyr Gly
                 85                  90                  95 cgc cag acc ctg acc cac gag atc ggc cat acc ctg ggc ctg agc cac        336
Arg Gln Thr Leu Thr His Glu Ile Gly His Thr Leu Gly Leu Ser His
            100                 105                 110 ccc ggc gac tac aac gcc ggc gag ggc gat ccc acc tac gcc gac gct        384
Pro Gly Asp Tyr Asn Ala Gly Glu Gly Asp Pro Thr Tyr Ala Asp Ala
            115                 120                 125 acc tac gcc gag gac acc cgc gcc tat tcg gtg atg agc tac tgg gaa        432
Thr Tyr Ala Glu Asp Thr Arg Ala Tyr Ser Val Met Ser Tyr Trp Glu
            130                 135                 140 gag cag aac acc ggc cag gac ttc aag ggc gcc tat tcc tcg gca ccg        480
Glu Gln Asn Thr Gly Gln Asp Phe Lys Gly Ala Tyr Ser Ser Ala Pro
145                 150                 155                 160 ctg ctg gac gac atc gcg gcg atc cag aag ctc tac ggg gcc aac ctg        528
Leu Leu Asp Asp Ile Ala Ala Ile Gln Lys Leu Tyr Gly Ala Asn Leu
                165                 170                 175 acc acc cgc acc ggc gac acg gtg tac ggc ttc aac tcc aac acc gag        576
Thr Thr Arg Thr Gly Asp Thr Val Tyr Gly Phe Asn Ser Asn Thr Glu
            180                 185                 190 cgc gac ttc tac agc gcc acc tcg tcc agt tcc aag ctg gtg ttc tcg        624
Arg Asp Phe Tyr Ser Ala Thr Ser Ser Ser Ser Lys Leu Val Phe Ser
            195                 200                 205 gtg tgg gac gcc ggc ggc aac gac acc ctg gac ttc tcc ggc ttc agc        672
Val Trp Asp Ala Gly Gly Asn Asp Thr Leu Asp Phe Ser Gly Phe Ser
210                 215                 220 cag aac cag aag atc aac ctc aac gag aag gcg ctg tcc gat gtc ggc        720
Gln Asn Gln Lys Ile Asn Leu Asn Glu Lys Ala Leu Ser Asp Val Gly
225                 230                 235                 240 ggg ttg aag ggc aat gtg tcg atc gct gcc ggg gtc acc gtg gaa aac        768
Gly Leu Lys Gly Asn Val Ser Ile Ala Ala Gly Val Thr Val Glu Asn
                245                 250                 255 gcc atc ggc ggc tcg ggt agc gac ctg ttg atc ggc aac gac gtg gcc        816
Ala Ile Gly Gly Ser Gly Ser Asp Leu Leu Ile Gly Asn Asp Val Ala
            260                 265                 270 aac gtg ctc aag ggc ggc gcc ggc aac gac atc ctc tac ggc ggc ctc        864
Asn Val Leu Lys Gly Gly Ala Gly Asn Asp Ile Leu Tyr Gly Gly Leu
            275                 280                 285 ggc gcg gac cag ctg tgg ggt ggc gcg gga gcc gac acc ttc gtc tac        912
Gly Ala Asp Gln Leu Trp Gly Gly Ala Gly Ala Asp Thr Phe Val Tyr
            290                 295                 300 ggc gat atc gcc gag tcc tcc gcg gcg gcg ccg gat acc ctg cgc gac        960
Gly Asp Ile Ala Glu Ser Ser Ala Ala Ala Pro Asp Thr Leu Arg Asp
305                 310                 315                 320 ttc gtc agc ggc cag gac aag atc gac ctg tcc ggg ctg gac gcc ttc       1008
```

```
                Phe Val Ser Gly Gln Asp Lys Ile Asp Leu Ser Gly Leu Asp Ala Phe
                                325                 330                 335 gtc aac ggc ggg ctg gtg ctg caa tac gtc gac gcc ttc gcc ggc aag         1056
Val Asn Gly Gly Leu Val Leu Gln Tyr Val Asp Ala Phe Ala Gly Lys
        340                 345                 350 gcc ggc cag gcg atc ctg tcc tac gac gcg agc aag gcc ggc agc             1104
Ala Gly Gln Ala Ile Leu Ser Tyr Asp Ala Ser Lys Ala Gly Ser
355                 360                 365 ctg gcg atc gac ttc agc ggg gac gcc cat gcc gat tcc gcg atc aat         1152
Leu Ala Ile Asp Phe Ser Gly Asp Ala His Ala Asp Phe Ala Ile Asn
        370                 375                 380 ctg atc ggc cag gcg acc cag gcc gac atc gtc gtc aga agc gat             1197
Leu Ile Gly Gln Ala Thr Gln Ala Asp Ile Val Val Arg Ser Asp
385                 390                 395 tgaggatatc acgtgggatc c                                                 1218

<210> SEQ ID NO 2
<211> LENGTH: 399
<212> TYPE: PRT
<213> ORGANISM: Leucosporidium antarcticum

<400> SEQUENCE: 2

Tyr Val Ser Asp Ile Tyr Ser Leu Gly Lys Phe Ser Ala Phe Ser Ala
1               5                   10                  15

Gln Gln Gln Ala Gln Ala Lys Ser Ser Leu Gln Ser Trp Ser Asp Val
            20                  25                  30

Thr Asn Ile His Phe Val Asp Ala Gly Gln Gly Asp Gln Gly Asp Leu
        35                  40                  45

Thr Phe Gly Asn Phe Ser Ser Val Gly Gly Ala Ala Phe Ala Phe
    50                  55                  60

Leu Pro Asp Val Pro Asp Ala Leu Lys Gly Gln Ser Trp Tyr Leu Ile
65                  70                  75                  80

Asn Ser Ser Tyr Ser Ala Asn Val Asn Pro Ala Asn Gly Asn Tyr Gly
                85                  90                  95

Arg Gln Thr Leu Thr His Glu Ile Gly His Thr Leu Gly Leu Ser His
            100                 105                 110

Pro Gly Asp Tyr Asn Ala Gly Glu Gly Asp Pro Thr Tyr Ala Asp Ala
        115                 120                 125

Thr Tyr Ala Glu Asp Thr Arg Ala Tyr Ser Val Met Ser Tyr Trp Glu
    130                 135                 140

Glu Gln Asn Thr Gly Gln Asp Phe Lys Gly Ala Tyr Ser Ser Ala Pro
145                 150                 155                 160

Leu Leu Asp Asp Ile Ala Ala Ile Gln Lys Leu Tyr Gly Ala Asn Leu
                165                 170                 175

Thr Thr Arg Thr Gly Asp Thr Val Tyr Gly Phe Asn Ser Asn Thr Glu
            180                 185                 190

Arg Asp Phe Tyr Ser Ala Thr Ser Ser Ser Lys Leu Val Phe Ser
        195                 200                 205

Val Trp Asp Ala Gly Gly Asn Asp Thr Leu Asp Phe Ser Gly Phe Ser
    210                 215                 220

Gln Asn Gln Lys Ile Asn Leu Asn Glu Lys Ala Leu Ser Asp Val Gly
225                 230                 235                 240

Gly Leu Lys Gly Asn Val Ser Ile Ala Ala Gly Val Thr Val Glu Asn
                245                 250                 255

Ala Ile Gly Gly Ser Gly Ser Asp Leu Leu Ile Gly Asn Asp Val Ala
            260                 265                 270
```

```
Asn Val Leu Lys Gly Gly Ala Gly Asn Asp Ile Leu Tyr Gly Gly Leu
        275                 280                 285

Gly Ala Asp Gln Leu Trp Gly Gly Ala Gly Ala Asp Thr Phe Val Tyr
    290                 295                 300

Gly Asp Ile Ala Glu Ser Ser Ala Ala Ala Pro Asp Thr Leu Arg Asp
305                 310                 315                 320

Phe Val Ser Gly Gln Asp Lys Ile Asp Leu Ser Gly Leu Asp Ala Phe
                325                 330                 335

Val Asn Gly Gly Leu Val Leu Gln Tyr Val Asp Ala Phe Ala Gly Lys
            340                 345                 350

Ala Gly Gln Ala Ile Leu Ser Tyr Asp Ala Ala Ser Lys Ala Gly Ser
        355                 360                 365

Leu Ala Ile Asp Phe Ser Gly Asp Ala His Ala Asp Phe Ala Ile Asn
    370                 375                 380

Leu Ile Gly Gln Ala Thr Gln Ala Asp Ile Val Val Arg Ser Asp
385                 390                 395

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgaattcgt cgacaacaga gtttgatcct ggctcag                              37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccgggatcc aagcttacgg ctaccttgtt acgactt                              37

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5
```

COLD ACTIVE ENZYME AND METHOD THEREOF

SEQUENCE LISTING

The instant application contains a Sequence Listing which has been submitted in ASCII format via EFS-Web and is hereby incorporated by reference in its entirety. Said ASCII copy, created on Dec. 6, 2010, is named 87144373.txt and is 10,370 bytes in size.

FIELD OF INVENTION

The present invention relates to the fields of enzyme technology and microbiology. More particularly, this invention relates to a process of producing a novel enzyme at low temperature. Moreover, the enzyme is isolated from a novel purified microorganism.

BACKGROUND OF THE INVENTION

Cold-adapted microorganisms, which are expected to produce cold-adapted enzymes, usually grow slowly even under appropriate conditions. Cold-adapted enzymes from psychrophilic microorganisms shows high catalytic activity at low temperatures can be highly expressed in such recombinant strains. Enzymes, which are proteins capable of catalyzing all the biochemical reactions occurring within an organism that render them compatible with life, are an essential target for the adaptation of an organism to a cold environment. Recently a systematic investigation has been carried out in order to understand the rules governing their molecular adaptation to low temperature. Psychrophilic enzymes have a high specific activity at low and moderate temperature and are inactivated easily by a moderate increase in temperature. In fact, many enzymes from psychrophiles correlate high catalytic activity and low thermal stability at moderate temperatures, which can be partly explained by the increased flexibility of the molecule, compared with mesophilic and thermophilic enzymes. The specific activity of wild type cold enzymes and some of their recombinant forms have been determined for several enzyme produced by Antarctic and Arctic microorganisms including α-amylase, protease, xylanase, lipase, citrate synthase and β-Lactamase. Esterase and lipases are the most widely used biocatalysts in fine chemical applications, largely because the advantages of these catalysts for the production of pure compounds. Lipases are produced by different microorganisms including yeast, fungi and bacteria. Lipases have been widely used for biotechnological and industrial applications such as in food industry, oil processing, production of surfactants, oil processing, detergents, pesticides, environmental management and leather industry.

The temperature stability of lipases has been regarded as the most important characteristic for use in industry. However, low stability is favorable for some purposes. For example, heat-labile enzymes can be easily inactivated by treatment for short periods at relatively low temperatures after being used for processing of food and other materials At present, only minor fractions of the microorganisms on Earth has been exploited. Novel developments in the cultivation and production of extremophiles and developments related to cloning and expression of genes in heterologous hosts will increase the number of enzyme-driven transformations in chemical, food, pharmaceutical and other industrial applications. Therefore, the objective of the present invention is to obtain a low temperature producing enzyme and more particularly, the enzyme provides a bifunctional purpose of varying its enzyme activity into activity of another enzyme. The present invention has overcome problems such as ability of obtaining an enzyme at low temperature. Accordingly, the present invention relates to LipPI12 as a novel cold active bifunctional lipase with protease activity, wherein the lipase was isolated from the cold continent of Antarctic microorganism. The benefits of the present invention include economic benefits in industry and biotechnology. Whereby the present invention reduces the requirement for expensive heating steps, provide increased reaction yields, accommodate a high level of stereospecificity, and minimize undesirable chemical reactions that can occur at higher temperatures. Furthermore, the present invention also exhibit thermal liability for rapidly inactivating the enzyme when required. In the distance future, a scale up production of LipPI12 and structural elucidation is recommended in-order to provide a better understanding of the exclusivity of the enzyme.

SUMMARY OF THE INVENTION

The present invention relates to a biologically pure culture of *Leucosporodium antarcticum* (preferably *Leucosporodium antarcticum* PI12 strain), is isolated from antarctic sea, deposited under the accession number NCYC number 3391 at the National Collection of Yeast Cultures (NCYC). The *Leucosporodium antarcticum* PI12 strain having the capability to produce a novel bifunctional enzyme (preferably a cold active lipase and known as LipPI12) isolated and characterized from a psychrophilic microorganism. Accordingly, the *Leucosporodium antarcticum* PI12 strain showing the characteristics that includes: a gram negative microorganism; having the capability to grow between 4° C. and 20° C.; showing a positive growth in LB media, tryptone soy media, skim milk agar, tributyrin gara, triolein agar, Rhodemine B agar, showing resistance ampicilin, kanamycin, chloramphenicol and streptomycin.

The novel bifunctional enzyme provides a function that is capable to produce a lipase and/or a protease enzyme. The lipase is produce at a temperature between 4 and 35° C. and protease is produce at a temperature between 4 and 45° C. It is understood that he lipase is LipPI12 encodes a nucleotide and deduced amino acid sequence of SEQ ID NO 1.

Accordingly, the novel bifunctional enzyme provides an identification under the SEQ ID NO 1 having an open reading frame (ORF) at least 783 bp and encodes for 260 amino acids.

Accordingly, the present invention also relates to a process of producing a bifunctional enzyme, wherein the bifunctional enzyme isolated and characterized from *Leucosporodium antarcticum* PI12 strain, wherein the process includes: obtaining *Leucosporodium antarcticum* PI12 strain; screening the strain for extracellular lipase activity at 4° C.; conducting a quantitative assay for cold active lipase activity; conducting a quantitative assay for protease activity; identifying and amplifying 16S rDNA sequence by conducting polymerase chain reaction (PCR) technique; obtaining a cold active lipase (LipPI12) gene by performing cloning (genomic library) technique; conducting intracellular expression of the cold active lipase gene and obtaining an expressed cold active lipase (LipPI12) gene; conducting extracellular expression of the cold active lipase gene and obtaining an expressed cold active lipase (LipPI12) gene; comparing between intracellular and extracellular of the LipPI12; purifying intracellular and extracellular of the LipPI12 and obtaining a purified LipPI12 lipase; determining size of protein; characterizing the cold active lipase (LipPI12) using biochemical and biophysical methods. In addition, the process further includes developing a three dimensional structure of LipPI12.

Indeed, the cold active lipase gene (LipPI12) provides the following characteristic such as having a working inducer (IPTG) between 0-0.5 mM; working incubation time between 0 and 40 hours; working inducer (IPTG) between 0-40 μM.

It is said that, the purified LipPI12 lipase having a size of 27 kDa and 3 kDa of His Tag.

Accordingly, the cold active lipase gene (LipPI12) having a melting point (Tm) between 5 and 70° C.

The present invention also describes a novel bifunctional enzyme of cold adapted LipPI12 obtained from *Leucosporodium antarcticum* PI12 strain, wherein the cold adapted LipPI12 includes a working temperature range from 5° C. to 40° C. with an optimum temperature at least 20° C. for lipase and 35-40° C. for protease, a working pH in the range of pH 4 to 12, working metal ions, the metal ions includes Na+, Mg+, $Ca^{2+}$, Fe2+, Mn2+, K+, Zn2+ and Cu2+, wherein the metal ions having the capability to treat the LipPI12 enzyme for at least 30 min at 20° C., working substrate, the substrate includes triglycerides, p-nitrophenol esters and natural oils, whereby the triglycerides; triacetin, tributyrin, tricapylin and triolein, whereby the p-nitrophenol esters includes; p-nitrophenylbutyrate, p-nitrophenylcaprylate, p-nitrophenyllaurate, p-nitrophenylpalmitate whereby the natural oils include: olive oil, soy bean oil, corn oil, sun flower oil, rice bran oil and palm oil.

Indeed, the LipPI12 provides a working inhibitors, the inhibitors includes: PMSF, EDTA and pepstatin wherein the inhibitors having the capability to treat the LipPI12 enzyme for at least 30 min at 20° C.

In addition, the LipPI12 offers a working organic solvents, wherein the organic solvents include: hexadecane, benzene, dodecane, heptane, hexane, decane heptanes, dimethylsulphonyl, hexadecane, toluene, ethybenzene, diethylether and a working surfactant includes TWEEN™ 20-80, TRITON™ X-100, SDS and SLS.

Finally, the present invention also describes the use of the bifunctional enzyme according to any of claims 1 to 17 for industrial applications such as in food industry, oil processing, production of surfactants, oil processing, detergents, pesticides, environmental management and leather industry.

DESCRIPTION OF THE DRAWINGS

FIG. 1 shows Microscopic structure of the microorganism PI12. The yeast like cells were stained via simple staining method. Each scale represents 0.01 mm. The individual cell was measured approximately at 0.02×0.04 mm.

FIG. 2 shows Clear halo formed on tributyrin agar plates. Isolate PI12 was grown on top of nutrient agar containing tributyrin for 7 days. Clearing zone indicates hydrolysis of tributyrin (C4). This indicates the presence of esterase. Further confirmation for lipase activity were done by plating on top Rhodamine B agar and Victoria blue agar plates.

FIG. 10 shows Fragment of the suspected lipase gene (~1.7 kb) electroeluted on 1% agarose. Lane 1: 1 kb DNA marker; Lane 2: Digested pRSET (2.9 kb) with insert.

FIG. 11: Nucleotide sequence and its deduced amino acids of LipPI12 comprising 780 nucleotides and 260 amino acids, respectively. FIG. 11 discloses the DNA sequence as SEQ ID NO: 1 and the PRT sequence as SEQ ID NO: 2.

FIG. 12 shows Effect of crude lipase activity at different temperatures. The crude recombinant cold active lipase was incubated at various temperatures from 5-40° C. and was assayed using olive oil as substrate.

FIG. 13 shows Expression profile of cold adapted lipase at different concentrations of IPTG. Lane 1: 0.025 mM; Lane 2: 0.05 mM; Lane 3: 0.1 mM and Lane 4; 0.3 mM. Lane 5: 0.5 mM; Lane 6: Protein molecular weight marker: β-galactosidase (116 kDa), bovine serum albumin (66.2 kDa), ovalbumin (45 kDa), lactate dehydrogenase (35 kDa), restriction endonuclease Bsp 981 (25 kDa), β-lactoglobulin (18.4 kDa) and lysozyme (14.4 kDa).

FIG. 14 shows Optimum concentration of IPTG for the intracellular expression of cold adapted lipase gene in *E. coli*. The recombinant *E. coli* habouring pTrchis2/LipPI12 gene were induced at $Abs_{600\ nm}$ ~0.5 from 0 to 0.5 mM of IPTG. The induced culture were grown at 20° C. for 24 hours FIG. 15 shows Effect of lipase expression at different time interval. The recombinant *E. coli* habouring pTrchis2/LipPI12 gene were induced at $Abs_{600\ nm}$ ~0.5. The cultures were induced using 0.3 mM of IPTG up to 40 h.

FIG. 16 shows Soluble and insoluble fractions of the recombinant lipase (indicated by the arrows). Odd numbered lanes: insoluble proteins; Even numbered lanes: soluble proteins; Lane 1,2: 0 h; Lane 3,4: 4 h; Lane 5,6: 8 h; Lane 7,8: 16 h; Lane 9,10: 24 h; Lane 11,12: 32 h; Lane 13,14: 40 h; M: Protein molecular weight marker: β-galactosidase (116 kDa); bovine serum albumin (66.2 kDa); ovalbumin (45 kDa), lactate dehydrogenase (35 kDa); restriction endonuclease Bsp 981 (25 kDa); β-lactoglobulin (18.4 kDa) and lysozyme (14.4 kDa).

FIG. 17 shows Optimization of IPTG concentration on secretory expression of recombinant cold adapted lipase. Induction of pBAD/LipPI12 was done using 0.02% (w/v) of L-arabinose whereby pJL3 plasmid were induced ranging from 0-0.06 mM of IPTG in order to optimize expression of bacteriocin release protein (BRP). Intracellular activity (□); extracellular activity (▨)

FIG. 18 shows The effect of intracellular and extracellular expressions at different L-arabinose concentrations. Recombinant E. coli Top10 containing pBAD/LipPI12 were induced using L-arabinose at different concentration ranging from 0-0.2% (w/v). Intracellular activity (□); extra-cellular activity (▨).

FIG. 19 shows Purification profile of the recombinant intracellularly expressed LipPI12 from affinity chromatography. Purification was done under native condition and LipPI12 was purified from a single step method. Lipase activity (▲); Protein content (♦).

FIG. 20 shows The SDS PAGE (A) and native PAGE (B) of the purified recombinant intracellularly expressed cold adapted LipPI12. Arrows indicate the purified protein with approximate size of ~30 kDa. Lane 1: Protein marker; Lane 2: Crude enzyme; Lane 3: Purified LipPI12.

FIG. 21 shows Purification profile of the recombinant extracellularly expressed cold adapted LipPI12 from affinity chromatography. Purification was done under native condition and LipPI12 was purified from a single step method. Lipase activity (■); Protein content (♦).

FIG. 22 shows Purified extracellularly expressed recombinant cold adapted LipPI12 electroeluted using SDS PAGE (stained via silver staining method). Lane 1: Protein marker, Lane 2: Crude enzyme, Lane 3: Purified LipPI12:

FIG. 23 shows Predicted model of the cold adapted lipase from *Leucosporodium antarcticum* sp. strain PI12.

FIG. 24 shows Optimum temperature profile of LipPI12 lipase and protease. Lipase and protease assays were done 20° C. using olive oil and azocasein as substrates respectively. Lipase activity (■); Protease activity (♦).

FIG. 25 shows pH profile of LipPI12 lipase. Acetate buffer (♦); potassium phosphate buffer (■); tris-HCl buffer (▲); glycine-NaOH buffer (−), $Na_2HPO_4$—NaOH.

FIG. 26 shows pH profile of LipPI12 protease. Acetate buffer (♦); potassium phosphate buffer (■); tris-HCl buffer (▲); glycine-NaOH buffer (−), $Na_2HPO_4$—NaOH.

FIG. 27 shows Effect of metal ions on LipPI12 lipase and protease activities. Both the lipase and protease were treated with 1 mM of various metal ions for 30 mins prior to enzyme assays. Lipase activity (▨); protease activity (▊).

FIG. 28 shows Effect of pure triglycerides on LipPI12 lipase activity. Values in bracket represent the carbon chain length of each substrate. LipPI12 lipase was assayed with the pure triglycerides (1:1, v/v) as substrate.

FIG. 29 shows Effect of various natural oils on LipPI12 lipase activity. Values in bracket represent the highest fatty acid component in the natural oil mixture. LipPI12 lipase was assayed with the natural oil (1:1, v/v) as substrate.

FIG. 30 shows LipPI12 hydrolysis profile on para-nitrophenyl esters. Values in bracket represent the fatty acid carbon chain length.

FIG. 31 shows Effect of various organic solvents on LipPI12 activity. Protease activity (▨); Lipase activity (▊).

FIG. 32 shows Thermostability profile of LipPI12 lipase. Activity at 15° C. (■); activity at 20° C. (♦).

FIG. 33 shows Thermostability profile of LipPI12 protease. Activity at 35° C. (■); activity at 40° C. (♦).

FIG. 34 shows Effect of various surfactants on both LipPI12 lipase and protease activities. The purified LipPI12 lipase and protease were mixed with surfactants (final concentration of 0.1%, v/v) and was incubated at 20° C. for 30 min prior to enzymatic assays. Lipase activity (▊); Protease activity (▨).

FIG. 35 shows Effect of inhibitors on LipPI12 lipase and protease activities. The final concentration of inhibitors was 1 mM. The LipPI12 lipase and protease were assayed with olive oil as substrate after incubation with inhibitors for 30 min. Lipase activity (▊); Protease activity (▨).

FIG. 36 shows hydrophobicity profile of LipPI12. The horizontal axis denotes the amino acid position from N to C terminal FIG. 37 shows melting point ($T_m$) determination of LipPI12, ranging from 5-70° C. The fitting lines and thermal bar are indicated in blue and red, respectively.

FIG. 38 shows Intrinsic value of LipPI12 fluorescence emission at various temperatures.

FIG. 39 shows Location of Trp (W) residue in LipPI12, shown from the predicted model.

FIG. 40 shows Intrinsic value of the LipPI12 fluorescence emission at various temperatures.

FIG. 41 shows Hydrophobic residues in LipPI12.

DESCRIPTION OF THE INVENTION

Figure 3:
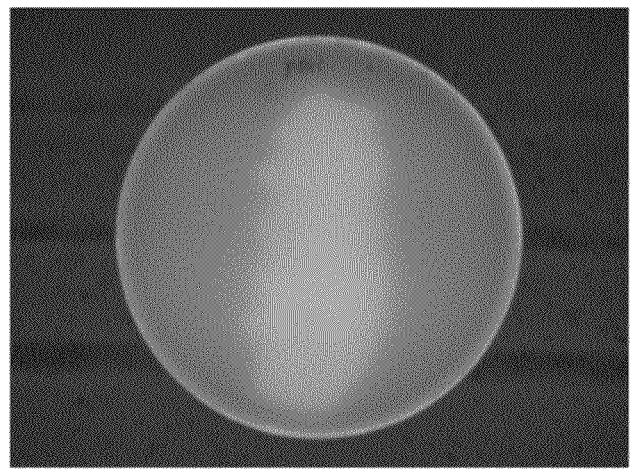
FIG. 3 shows Orange fluorescent formed around the colonies on top of rhodamine B agar. The free fatty acid interaction with rhodamine B dye was viewed under uv light which exhibit the orange fluorescence indicating the presence of lipase.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. It must be noted that as used herein and in the appended claims, the singular forms "a," "an," and "the" include plural referents unless the context clearly dictates otherwise.

The invention discloses a low-temperature lipase and its code gene and application. The invention also discloses a method for expressing low-temperature lipase (cold active lipase) in an engineered bacteria and method for preparing low-temperature lipase by using said engineering bacteria. The activity and stability of low-temperature lipase (preferably LipPI12 lipase) at low temperature, and can be used in fields of washing agent industry, foodstuff industry, biological pharmacy and environmental biological technique. Moreover, the present invention also describes on the LipPI12 lipase provides a protease activity, preferably when the lipase is at lower temperature, the lipase (LipPI12) reacts as a lipase and when it is at a high temperature the lipase changes to develop in protease, and being capable of developing into a protease activity. However, the LipPI12 lipase and the protease has shown to have different profile of activity.

INDUSTRIAL APPLICATION

In a process of producing a product, LipPI12 holds greater potentials in industrial application which mainly trying to focus on reducing energy as well as time and money. The enzyme will be a good addition to the enzyme sales as it is applied in dairy, detergents, pulp and papers, pharmaceuticals industries and many more. Temperature confer a huge role in industrial processes as today, high temperature reaction dominates. Nonetheless, it proved to be costly. Therefore, by shifting to low temperature application, the results will appear and at the same reducing the need for energy in heating purposes.

```
                                                  SEQ ID NOS 1 and 2
tatgtcagcgatatctactcgctgggcaagttcagcgccttttccgcgcagcagcaggcc
 Y  V  S  D  I  Y  S  L  G  K  F  S  A  F  S  A  Q  Q  Q  A caggccaagtcgtcgctgcaatcctggtcggacgtcaccaatatccacttcgtcgacgcc
 Q  A  K  S  S  L  Q  S  W  S  D  V  T  N  I  H  F  V  D  A ggccagggcgatcagggcgacctgaccttcggcaacttcagcagtagtgtcggcggtgcg
 G  Q  G  D  Q  G  D  L  T  F  G  N  F  S  S  S  V  G  G  A gcgttcgccttcctgccggatgtaccggatgcgctcaaggggcaatcctggtacctgatc
 A  F  A  F  L  P  D  V  P  D  A  L  K  G  Q  S  W  Y  L  I aacagcagctacagcgccaacgtcaatccggccaacggcaactacggacgccagaccctg
 N  S  S  Y  S  A  N  V  N  P  A  N  G  N  Y  G  R  Q  T  L acccacgagatcggccataccctgggcctgagccaccccggcgactacaacgccggcgag
 T  H  E  I  G  H  T  L  G  L  S  H  P  G  D  Y  N  A  G  E ggcgatcccacctacgccgacgctacctacgccgaggacacccgcgcctattcggtgatg
 G  D  P  T  Y  A  D  A  T  Y  A  E  D  T  R  A  Y  S  V  M agctactgggaagagcagaacaccggccaggacttcaagggcgcctattcctcggcaccg
 S  Y  W  E  E  Q  N  T  G  Q  D  F  K  G  A  Y  S  S  A  P ctgctggacgacatcgcggcgatccagaagctctacggggccaacctgaccacccgcacc
 L  L  D  D  I  A  A  I  Q  K  L  Y  G  A  N  L  T  T  R  T ggcgacacggtgtacggcttcaactccaacaccgagcgcgacttctacagcgccacctcg
 G  D  T  V  Y  G  F  N  S  N  T  E  R  D  F  Y  S  A  T  S tccagttccaagctggtgttctcggtgtgggacgccggcggcaacgacaccctggacttc
 S  S  S  K  L  V  F  S  V  W  D  A  G  G  N  D  T  L  D  F tccggcttcagccagaaccagaagatcaacctcaacgagaaggcgctgtccgatgtcggc
 S  G  F  S  Q  N  Q  K  I  N  L  N  E  K  A  L  S  D  V  G gggttgaagggcaatgtgtcgatcgctgccggggtcaccgtggaaaacgccatcggcggc
 G  L  K  G  N  V  S  I  A  A  G  V  T  V  E  N  A  I  G  G tcgggtagcgacctgttgatcggcaacgacgtggccaacgtgctcaagggcggcgccggc
 S  G  S  D  L  L  I  G  N  D  V  A  N  V  L  K  G  G  A  G aacgacatcctctacggcggcctcggcgcggaccagctgtggggtggcgcgggagccgac
 N  D  I  L  Y  G  G  L  G  A  D  Q  L  W  G  G  A  G  A  D accttcgtctacggcgatatcgccgagtcctccgcggcggcgccggatacctgcgcgac
 T  F  V  Y  G  D  I  A  E  S  S  A  A  A  P  D  T  L  R  D ttcgtcagcggccaggacaagatcgacctgtccgggctggacgccttcgtcaacggcggg
 F  V  S  G  Q  D  K  I  D  L  S  G  L  D  A  F  V  N  G  G ctggtgctgcaatacgtcgacgccttcgccggcaaggccggccaggcgatcctgtcctac
 L  V  L  Q  Y  V  D  A  F  A  G  K  A  G  Q  A  I  L  S  Y gacgcggcgagcaaggccggcagcctggcgatcgacttcagcggggacgcccatgccgat
 D  A  A  S  K  A  G  S  L  A  I  D  F  S  G  D  A  H  A  D ttcgcgatcaatctgatcggccaggcgacccaggccgacatcgtcgtcagaagcgattga
 F  A  I  N  L  I  G  Q  A  T  Q  A  D  I  V  V  R  S  D  - ggatatcacgtgggatcc
 G  Y  H  V  G  S
```

BEST MODE FOR CARRYING OUT THE INVENTION

In the context of the present invention, provides a screening and isolation of psychrophilic lipase producing microorganism, identifying the psychrophilic microorganism, cloning and sequencing the cold adapted lipase gene, expressing the cloned gene in *E. coli*, purifying of the recombinant lipase and characterizing of purified enzyme via biochemical and biophysical methods. A preferred embodiment of the present invention relates to cold adapted lipase of *Leucosporodium antarcticum* PI12 was successfully isolated via shotgun cloning. Several positive *E. coli* transformants were able to hydrolyze tributyrin on top of tributyrin agar plate containing ampicilin even at 4° C. Recombinant plasmid pRSET/PI12lipase was found to harbour a 1.6 kb insert containing one functional open reading frame (ORF) denotes as LipPI12. The open reading frame contains 783 nucleotides encoding 260 amino acids. Accordingly, optimum expression was achieved at 0.3 mM IPTG as inducer and after 32 hours of post induction time. Temperature is an essential aspect for expression of cold adapted enzyme and having said that, 20° C. was the optimal post induction growth temperature to express LipPI12 enzyme. Indeed, the formation of inclusion bodies remains to be the limiting factor. The cold adapted lipase was modeled using MODELLER 1.1 using the template of psychrophilic protease from *Pseudomonas* sp. TACII18. The putative 3D structure of the enzyme showed the typical properties of psychrophilic enzyme, which having an increasing number of loops and a non compact structure to cater the lipase structural flexibility. In the present invention, the cold adapted LipPI12 was successfully purified to homogeneity with the size ~30 kpa. Purified intracellularly expressed LipPI12 was recovered 75% with purification factor of 42. In addition, this present invention also describes LipPI12 expressed extracellular and further exhibited a same size with recovery and fold of 82% and 8.12 respectively. Characterization of the bifunctional ability of the LipPI12 in terms of optimum temperature showed the lipase has the optimum activity at 20° C. and protease was activated at higher temperature of 40° C. As for the pH, the recombinant LipPI12 showed an activity at pH 7 and pH 8 for lipase and protease respectively. Effect of metal ion on the other hand showed a different profile with $CaCl_2$ serves as its activator whereas $ZnCl_2$ and $MgCl_2$ as protease activator. Substrate specificity profile for LipPI12 showed that the lipase preferred medium chain length of fatty acids (C12). Both lipase and protease had shown some tolerance to organic solvents whereby the lipase was activated with solvents of high log P and interestingly the protease reacts vise versa. LipPI12 protease was activated in the presence of TWEEN™ 80 and SLS with 30 and 70% enhancement respectively. LipPI12 lipase also retains its activity when tested with TWEEN™ 40, 60 and TRITON™ X-100 compared to the total inhibition effect of TWEEN™ 20. Incubation with SDS has also an influence on LipPI12 catalytic activity whereby, it drops until 27% of its remaining activity. Accordingly, inhibitor used in the present invention revealed that LipPI12 lipase was partially inhibited with EDTA and PMSF whereby the LipPI12 protease was inhibited by pepstatin and was also partially inhibited by EDTA and PMSF Amino acid comparison also showed patterns of cold adaptation with increased glycine and proline ratio as temperature profile increased. LipPI12 also showed a decreased of arginine and lysine content which improved psychrophilicity.

In another preferred embodiment of the present invention relates to circular dichroism analysis, wherein in this analysis it showed, that a melting point of 38° C. In the Fluorescence spectroscopy analysis, revealed that LipPI12 posed a flexible structure with less hydrophobic core as shown from both intrinsic and extrinsic values. Characterization of LipPI12 has in fact shown some convincing results that the LipPI12 is cold tolerant. Ideally, it could serve as a good representation to enrich the knowledge on protein structure and functions. The findings of novel psychrophilic lipase LipPI12 with proteolytic activity dictates the convergence of lipase and protease or perhaps other enzymes from psychrophile, is also an adaptation to survive low temperature environment.

EXAMPLES

Sources of the Psychrophilic Microorganism

Few microbial isolates were taken from Antarctic sea ice near Casey station, Antarctica. Some of the isolates were able to grow at 4° C. and were screened for cold active lipolytic activity. Among these isolates, stain PI12 exhibited highest lipolytic activity and was then used for further investigation. Work involved microbial identification, lipase gene isolation, expression and purification of recombinant enzyme and also biochemical and biophysical characterization of the recombinant cold active lipase.

The bacterium was grown in nutrient broth and agar plates at 4° C. without shaking. Visible growth was observed after one week of incubation. The bacterium exhibited a yeast-like shape due to its budding properties and possession of a Gram negative cell wall commonly seen in other proteobacterial groups (FIG. 1). The growth of isolate PI12 was inhibited at 25-37° C.

Extracellular enzyme activities, by isolate PI12 namely protease and lipase, were also observed. Isolate PI12 exhibited a broad spectrum of resistance towards ampicilin, kanamycin and chloramphenicol, which is generally a typical characteristic possessed by Gram negative proteobacterium. The properties of the bacterium are shown in Table 1.

TABLE 1

| Characterization of psychrophilic microorganism PI12 | |
|---|---|
| Morphology | |
| Shape | Yeast like |
| Gram stain | Negative |
| Spore | − |
| Motility | + |
| Biochemical tests | |
| LB broth and agar | + |
| Tryptone soy broth and agar | + |
| Skim milk agar (protease) | + |
| Tributyrin agar (lipase) | + |
| Triolein agar (lipase) | + |
| Rhodamine B agar (lipase) | + |
| Pseudomonas agar (Fluorocein) | − |
| Ampicilin | + |
| Kanamycin | + |
| Chloramphenicol | + |
| Streptomycin | + |
| Microbial growth at: | |
| 37° C. | − |
| 4° C. | + |

Note:
+ (positive results);
− (negative results)

Screening for Extracellular Lipase

Figure 4:
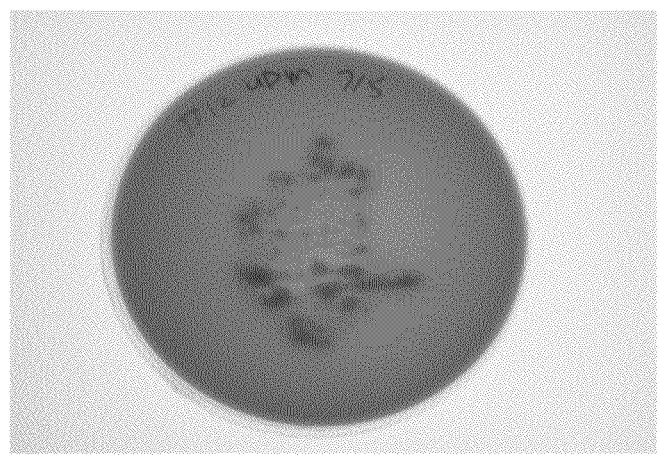
FIG. 4 shows Intense blue colour formed around the colonies. Increased acidity as a result of increased fatty acid favours the formation of more intensed blue colouration around the colony. The screening plate serves as alternative to the rhodamine B agar plates.

Extracellular lipase activity was determined using both qualitative and quantitative methods. Screening plates, namely tributyrin, Rhodamine B and triolein were used to carry out the experiment. Clearing zones were formed on tributyrin plates showed an extracellular lipase activity (FIG. 2). Free fatty acids, liberated by the lipase, react on the colouring dyes in both Rhodamine B and triolein plates containing Victoria blue, forming an orange fluorescent (FIG. 3) and intense blue colour for respective plates. (FIG. 4). The formation of the blue zones, on top of the triolein plates, is a result of the pH reduction of the medium due to the increased fatty acid compounds (Samad et al., 1989). Meanwhile, the exhibition of orange fluorescence is resulted by the formation of Rhodamine B-free fatty acid complex (Kouker and Jaeger, 1987). The bacterium was incubated at 4° C. for 7 days.

Quantitative Assay for Cold Active Lipase Activity

Lipase assay was done by using a simple and rapid colorimetric method by Kwon and Rhee (1986). The reaction mixture comprised 1.0 ml of enzyme, 2.5 ml olive oil emulsion (50% olive oil+50% phosphate buffer) and 0.02 ml $CaCl_2 2H_2O$. The reaction mixture was incubated for 30 minutes with the shaking rates at 400 rpm at 4° C. The reaction was stopped by adding 5.0 ml isooctane. The upper layer (4.0 ml) was pipetted out in a test tube and 1.0 ml of cupric acetate pyridine was added and the free fatty acid dissolved in isooctane were determined by measuring the absorbency of isooctane solution at 715 nm. Lipase activity was determined by measuring the amount FFA (free fatty acid) from the standard curve. One unit of lipase activity was defined as 1 µmole of fatty acid liberated per min under standard assay condition. It is said to be that the Lipase activity was at 0.051 U/ml when assayed at 4° C.

Quantitative Assay for Protease Activity

The protease assay was done by the modified method of Brock et al., (1982). The reaction mixture consist of 1 ml 0.5% (w/v) azocasein dissolved in 50 mM phosphate buffer pH 7.0 was preincubated in vial bottle at 30° C. for 30 minutes. The reaction was started by addition of 200 µl of enzyme solution and incubated 30° C. for 30 minutes in water bath. The enzyme reaction was then terminated by the addition of equivalent volume of 10% (v/v) TCA and vortex for 10 seconds. The mixture was then transferred to eppendorf tube and centrifuged at 14,000 rpm for 10 minutes. After the centrifugation process, the clear supernatant was mixed with an equal volume of 1M NaOH and the absorbance was read at 450 nm. For control, the same procedure was prepared and carried out. The enzyme was added at the end of the incubation process and was immediately terminated. One unit of activity (U) was defined as the rate of enzyme activity that produces an increase of absorbance (0.001/min) at the specified assay condition.

Preparation of Stock Culture

One loop full of culture from the stock slant was inoculated aseptically into 10 ml sterilized nutrient broth and incubated for 7 days at 4° C. The cultures were then streaked onto nutrient agar plates and were incubated for 7 days at 4° C. Only single colony was choosen and transferred onto nutrient agar slants. The slant serves as working culture throughout the project.

Genomic DNA Extraction and Microbial Identification

Figure 5:
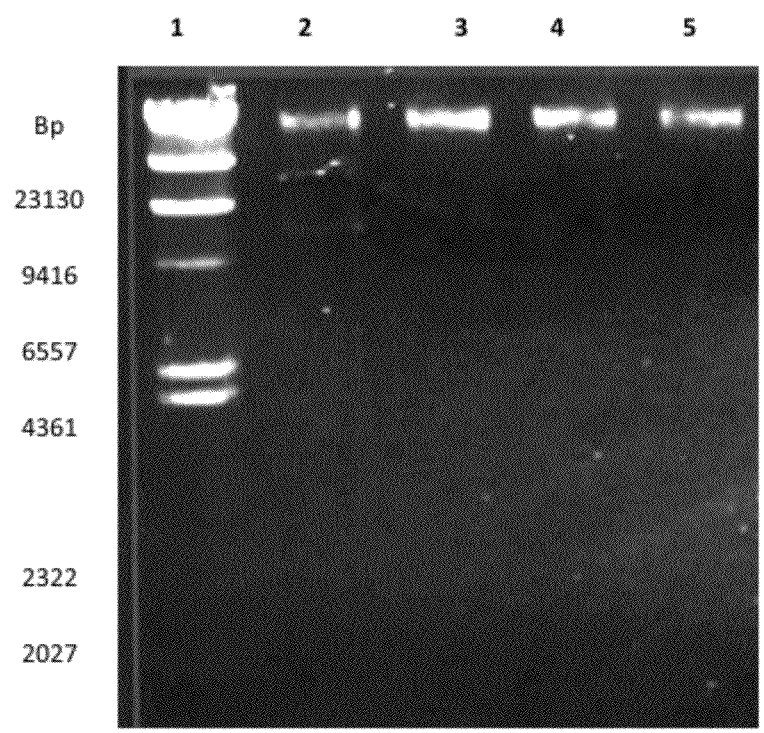
FIG. 5 shows Genomic DNA of isolate PI12 electrophoresed on 1% agarose gel Lane 1: Lambda HindIII marker; Lanes 2-5: Genomic DNA.

Genomic DNA of PI12 (FIG. 5) was manipulated using a protocol so as to isolate genomic DNA from the gram negative bacteria provided by QIAGEN. In order to identify the isolated microorganism, 16S rRNA sequencing was carried out.

Figure 6:
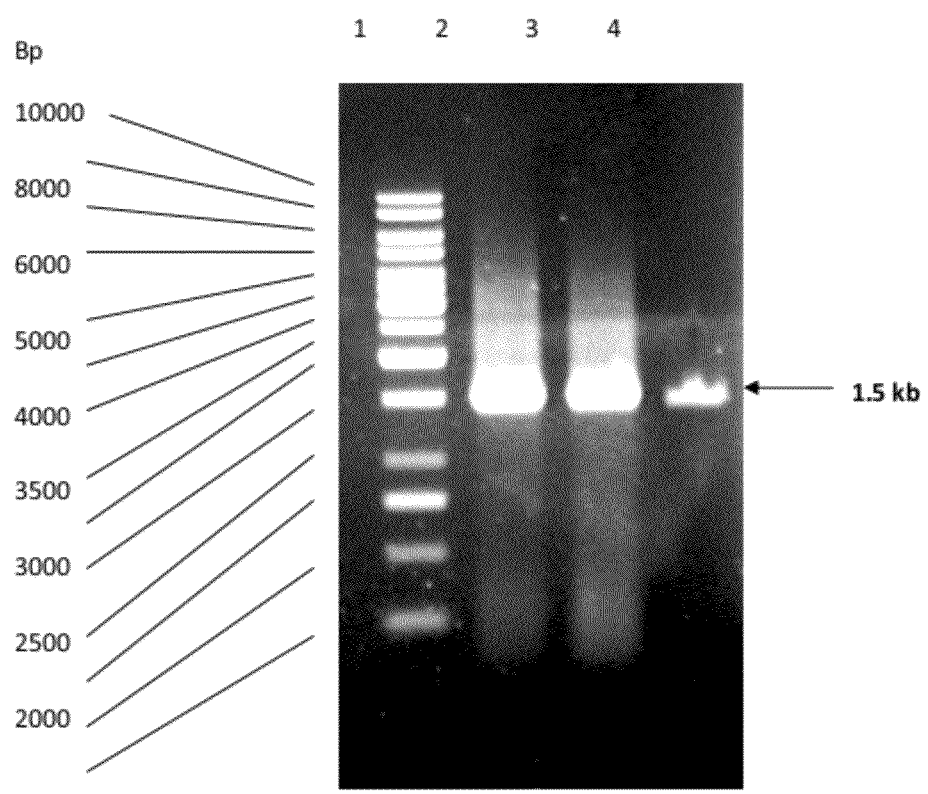
FIG. 6 shows PCR product electroeluted on 1% agarose. Lane 1: 1 kb DNA ladder; Lanes 2-4: PCR product of the 16S rRNA gene.

16S rRNA Sequence Identification 16S rRNA sequence was amplified via polymerase chain reaction (PCR) using two degenerated set of primers: Forward: 5'-CCGAATTCGTCGACAACAGAGTTTGATC-CTGGCTCAG-3' and reverse: 5'-CCCGGGATCCAAGCT-TACGGCTACCTTGTTACGACTT-3'. These primers amplified the 1.5 kb of PCR product. PCR was carried out in 100 µl mixture containing 1.5 mM $MgCl_2$. 1×PCR buffer, 0.2 mM dNTP mix, 2 unit of Taq DNA Polymerase, 10 pmol of each forward and reverse primers and genomic DNA (50-100 ng). After 3 minutes at 94° C., 30 PCR cycles (94° C.; 1 minute, 58° C.; 2 minutes and 72° C.; 2 minutes) were performed. This is followed by 1 cycle of 7 minutes at 72° C. and hold at 4° C. The reaction was amplified in a thermocycler (GeneAmp PCR System 2400, Perkin Elmer, Foste, Calif.). The amplified product were examined by electrophoresis and the PCR products were ligated into pDRIVE cloning vector (Qiagen) according the manufacturers protocols. After transformation into *E. coli*, the plasmid s were extracted and sequenced. Apparent homology search was performed with Genbank database (www.ncbi.nih.gov). A 1.5 kb PCR (FIG. 6) fragment was legated into the pDRIVE vector (Qiagen). *E. coli* Top10 was used as a cloning host.

Figure 7:
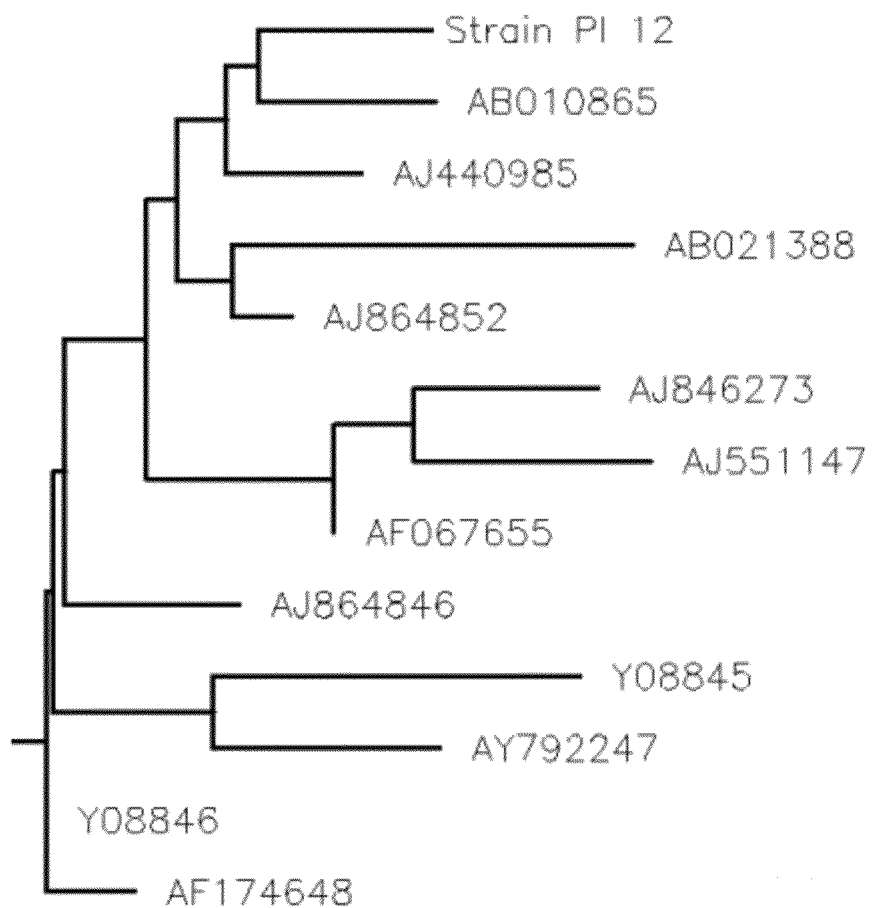
FIG. 7 shows Phylogenetic tree construction involving other 16S rRNA gene sequences of Gram negative bacteria. The cloned 16S rRNA gene was sequenced and the most likely bacteria to share the highest homology were taken into consideration in the phylogenetic tree. Microorganisms, assigned at each accession number, are as follows: *Beta proteobacterium* HTC018 (AB010865), *Antarctic bacterium* R-7687 (AJ440985), *Pseudomonas mephitica* (AB021388), *Janthinobacterium* sp. HHS32 (AJ846273), *Janthinobacterium* sp. An8 (AJ551147), Uncultured *Duganella* clone CTHB-18 (AF067655), *Janthinobacterium* sp. J43 (AJ864852), *Janthinobacterium lividum* (Y08846), Uncultured *beta proteobacterium* clone CrystalBog2KF8 (AY792247), *Janthinobacterium agaricidamnosum* (Y08845) and *Janthinobacterium lividum* (AF174648).

Molecular Identification and Phylogenetic Tree Analysis 16S rRNA gene, a large polynucleotide (~1500 bp) which functions as a part of the small sub-unit ribosome of prokaryotes, was used as taxanomical and phylogenetic tree analysis. Various micro-organisms, mainly from the proteobacterial groups, were gathered from the NCBI database, compared and aligned together, using the CLUSTAL W program (www-.workbench.sdsc.edu). An almost maximum homology of 99%, with other Gram negative bacteria, predominantly the *Janthinobacterium* sp. was obtained. The phylogram was then constructed, as depicted in FIG. 7. In-depth studies by Alias (2008; unpublished data) revealed that the isolate PI12 is a *Leucosporodium antarcticum*, based on the molecular analysis of the internal transcribe region (ITS) and 18S rDNA. The yeast-like shape of PI12, which was previously understood as PI12 bacterial morphology, is actually a typical yeast structure. The unique characteristic of the isolate PI12 could probably be caused by a mixture of genes, as a result of evolution where life which existed earlier was a simple entity. As a result of the environmental pressure, prokaryotic organism is engulfed by the higher eukaryotic micro-organism and lives as endosymbiont; gradually, the endosymbiosis creates a complex organism. Thus, this explains the mixed characteristics of the isolate PI12 or *Leucosporodium antarcticum*.

Cloning of the Cold Active Lipase Gene

Genomic DNA Extraction

Genomic DNA of PI12 was extracted using DNeasy tissue kit from Qiagen. Bacterial cells pellet from 10 ml of culture was resuspended in 180 µl ATL buffer. 20 µl of Proteinase K was added and mixed by vortexing and incubated at 55° C. until the cells were completely lysed. These followed by Rnase A treatment of the sample, where 4 µl of Rnase A (100 mg/ml) was added and mixed by vortexing and incubated for 2 minutes at room temperature. This sample will once again undergo vortexing for 15 s before 200 µl of AL buffer was added to the sample and mixed by vortexing and incubated 70° C. for 10 minutes. 200 µl of ethanol (96-100%) was added to precipitate the sample. The mixture was pipetted out into DNeasy spin column and centrifuged at 8000 rpm for 1 minute. The flow through was discarded. Buffer AW1 (500 µl) was added and been centrifuged for 1 minute at 8000 rpm and the flow through was discarded. Buffer AW2 (500 µl) was added and centrifuged for 3 minutes at full speed to dry the DNeasy membrane. The flow through was discarded. DNeasy spin column was placed in a 1.5 ml microcentrifuge tube and 200 µl buffer AE was pipetted onto the DNeasy membrane and incubated at room temperature for 1 minute. The sample was centrifuged for 1 minute at 8000 rpm for elution.

Quantification and Quality Assessment of Genomic DNA

An aliquot of the genomic DNA (5 μl) was diluted in 995 μl distilled water or TE buffer to give a final volume of 1000 μl Absorbance of the DNA at 260 nm and 280 nm was measured. The ratio of $A_{260}$ and $A_{280}$ was calculated. The value of pure DNA sample should be in the range of 1.8 to 2.0. A lower ratio is an indication of protein contamination. A DNA solution with $A_{260}$ of 1 contains approximately 50 μg/ml of DNA. Therefore, concentration of DNA can be calculated according to the following formula: Concentration of DNA (μg/ml)= A260×50 μg/ml×dilution factor.

Partial Digestion of DNA Using Sau3A1 for Genomic Library Construction

In order to prepare a clonable size of genomic DNA, small scale reactions were carried out to digest the DNA into 2 to 10 kb fragments. The restriction enzyme, Sau3A1 was diluted into ten different concentrations on ice (Table 4). After the dilutions have been made, small scale reactions were constructed by adding genomic DNA (5 μg), 10× reaction buffer (1.5 μg), Sau3A1 dilution (5 μl) and addition of distilled water up to 15 μl. All ten reactions were incubated at 37° C. for 30 minutes. The reactions were heat deactivated by incubating for 20 minutes at 65° C. the reaction mixture were mixed with 10 μl tracking dye (50% w/v glycerol, 0.1 M EDTA, 1% w/v SDS, 0.1% w/v bromophenol blue) and loaded into 1% w/v agarose gel. Gel electrophoresis were carried out at 90 V for 1 hour to determined the concentration of Sau3A1 to produced the desired DNA size ranged 2 to 10 kb. After determining the appropriate concentration of Sau3A1 to use, a large scale partial digestion was performed. The reaction was scaled up to 10 times and digested with one half of the desired enzyme concentration, which was previously determined. After digestion, the cleaved DNAs in the range of 2 to 10 kb was excised from the gel and purified.

TABLE 2

Dilutions of Sau3A1 in ten individual microcentrifuge tubes (Adapted from Wu et al., 1997)

| Tube | Sau3A1 (3U/μl) Dilution | Dilution Factors |
|---|---|---|
| 1. 2 μl Sau3A1 | +28 μl 1X Sau3A1 buffer | 1/15 |
| 2. 10 μl of 1/15 dilution | +90 μl 1X Sau3A1 buffer | 1/150 |
| 3. 10 μl of 1/150 dilution | +10 μl 1X Sau3A1 buffer | 1/300 |
| 4. 10 μl of 1/150 dilution | +30 μl 1X Sau3A1 buffer | 1/600 |
| 5. 10 μl of 1/150 dilution | +50 μl 1X Sau3A1 buffer | 1/900 |
| 6. 10 μl of 1/150 dilution | +70 μl 1X Sau3A1 buffer | 1/1200 |
| 7. 10 μl of 1/150 dilution | +90 μl 1X Sau3A1 buffer | 1/1500 |
| 8. 10 μl of 1/150 dilution | +110 μl 1X Sau3A1 buffer | 1/1800 |
| 9. 10 μl of 1/150 dilution | +190 μl 1X Sau3A1 buffer | 1/3000 |
| 10. 10 μl of 1/150 dilution | +290 μl 1X Sau3A1 buffer | 1/4500 |

Genomic Library Construction

Figure 8:
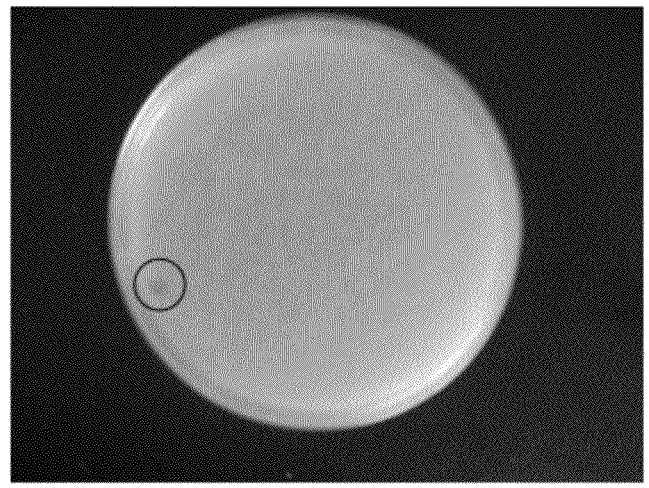
FIG. 8 shows One of the positive transformants (circled area) harbouring the putative lipase gene. Thousands of recombinant *E. coli* were plated on top of LB agar containing tributyrin and ampicilin for easy identification of recombinant clones containing putative lipase gene.
Figure 9:
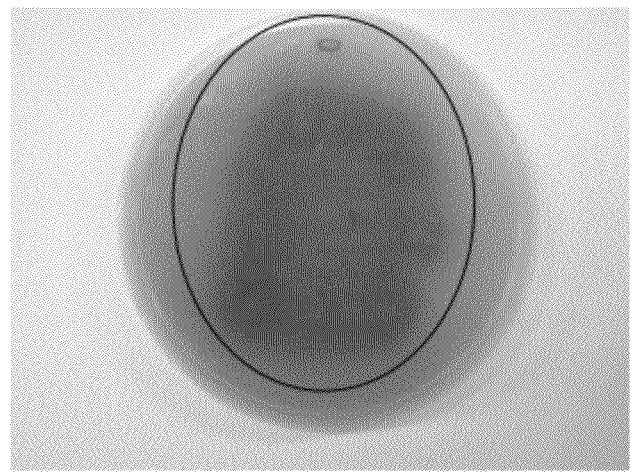
FIG. 9 shows Intensive blue colouration inside the circled area denoting putative pLipPI12 formed on top of the LB agar containing triolein and ampicillin.

Among thousands of transformants from the shotgun cloning, four of them produced clearing zone. The positive recombinant, harbouring the suspected lipase, was assumed to have cold active lipolytic activity when the recombinant clone was initially grown at 37° C. for 24 hours and transferred at 4° C. The clearing zone appeared after 3 days of incubation at 4° C. (FIG. 8). The colonies were transferred to a more selective media, i.e. the triolein plates, to confirm the lipase gene expression, as illustrated in FIG. 10. The blue colouration, which was formed in the low temperature on top of LB trio lein plates, was an indication that *E. coli* had harboured a lipase gene. The transformant was subjected to lipase assay, using olive oil as substrate and found to have a lipase activity of 0.106 U/ml, at a temperature as low as 4° C. The enzyme was expressed at 3.5 folds higher than its wild type strain, bacterium PI12. The lipase was believed to be cold adapted/ active and would probably possess one or more properties, which enabled this enzyme to be cold tolerant. This called for further investigations of the gene and its function.

Plasmid DNA (pRSET) Extraction

Plasmid pRSET C was extracted by QIAprep Spin Miniprep Kit from Qiagen. Cells harboring the plasmid were grown in LB broth containing ampicilin (50 μl/mg) for 16 hours and pelleted by centrifugation. The cell pellet was resuspended in 250 μl of Buffer P1. 250 μl of Buffer P2 was added and gently mixed. This followed by addition of 350 μl of Buffer N3. The tube was inverted for several times before being centrifuged at 14000 rpm for 10 minutes. The supernatant was transferred to the QIAprep column by pipetting and being centrifuged for 30 to 60 s. The flow through was discarded. The QIAprep column was washed by adding 0.5 ml Buffer PB and centrifuged for 30 to 60 s and the flow through was discarded. The QIAprep column was washed by adding 0.75 ml Buffer PE and centrifuging for 30 to 60 s. The flow through was discarded and centrifuged for an additional 1 minute to removed residual wash buffer. The QIAprep was placed in a clean 1.5 ml microcentrifuge tube and DNA was eluted by adding 50 μl Buffer EB (10 mM Tris.Cl, pH 8.5) to the center of the QIAprep column, stand for 1 minute and centrifuged for 1 minute. The sample was loaded on agarose gel (1% w/v) to detect the molecular weight of the extracted plasmid.

Restriction Enzyme Digestion and Dephosphorylation of pRSET

The plasmid was digested with BamH1 in order to generate compatible ends for ligation with Sau3A1 partially digested genomic DNA. The plasmid DNAs (50 μl) was digested with BamH1 for 1 hour in a 100 μl reaction mixture: distilled water (37 μl), 10× buffer E (10 mM Tris-HCl, pH 7.4, 300 mM KCl, 5 mM $MgCl_2$, 0.1 mM Dithiothreitol, DTT (10 μl), BSA (0.1 μl; 1 μl), DNA (50 μl), and enzyme (10 U; 2 μl). The mixture was incubated at 37° C. for 1 hour. 10 microliter of the reaction mixture was the loaded in agarose gel (1% w/v) to confirmed complete digestion. The cleaved products were dephosphorylated by directed addition of calf intestinal alkaline phosphatase (1 U, 1 μl) for 1 hour at 37° C. The enzyme was deactivated by heating at 65° C. for 20 minutes with the presence of EDTA (5 mM).

Ligation of Sau3A1 Partially Digested Genomic DNAs with BamH1 Digested pRSET

The Sau3A1 partially digested genomic DNAs with maximum intensity of DNA size in the range of 2-9 kb were ligated with pUC19 (BamH1 digested and dephosphorylated). DNA ligase was used to join the Sau3A1 and BamH1 digested cohesive ends. The ligation mixture: pRSET (0.5 μg), Sau3A1 partially digested DNA (1 μg), 10× ligase buffer (300 mM Tris-HCl pH 7.8, 100 mM $MgCl_2$, 100 mM DTT, 10 mM ATP; 1.5 μl), T4 DNA ligase (Promega, Madison, Wis. 5 U, 1 μl), $dH_2O$, top up to 15 μl) was prepared for 16 hours at 16° C.

Preparation of Competent Cell and Transformation

A single colony of *E. coli* Top10 cells from a fresh LB agar was inoculated into 10 ml LB broth with shaking rates at 150 rpm at 37° C. until an $A_{600}$ of 0.4-0.5 was obtained. The cell were pelleted at 5000×g for 15 minutes at 4° C. gently resuspended in a 1/12 volume of ice cold Calcium/Manganese based buffer (CCMB) and placed on ice for 1 hour. The CCMB treated cells were pelleted again at 5000 rpm for 15 minutes. The supernatant was discarded and the cells were gently resuspended in 1/3 of ice cold CCMB buffer. The competent cells (100 μl) were aliquoted into sterilized microcentrifuged tubes and kept in −80° C. Transformation of *E. coli* was performed according to the method describe by Sambrook et al., (1985). The ligation mixture (5 µl) was transferred to competent cells (100 µl) and placed on ice for 15 minutes. The tubes were placed at 42° C. for 2 minutes followed by chilling briefly on ice. The transformed cells were transferred to growth medium called SOC (250 µl) and incubated for 1 hour at 37° C. with shaking at 150 rpm. Then, the transformation cultures were (30 µl, 50 µl, and 100 µl) plated onto separated Tributyrin-Ampicilin agar and was further incubated at 37° C. Tributyrin-Amp agar was supplemented with isopropyl-β-D-thiogalactopyranoside (IPTG) with the concentration of 1M (5 µl) and X-gal (2% w/v, 50 µl) by spreading on the agar 30 minutes before transferring the transformation culture on the agar.

Screening for Positive Recombinant Clones

Putative lipase activity was indicated by the formation of halo on the tributyrin-amp agar around the colonies. Cold active lipase activity was conferred by incubating the plates at 37° C. for 24 hours and another 3 of incubation at 4° C. Colonies that produced clearing zone on tributyrin-amp agar were isolated and restreaked on triolein-amp agar. Formation of blue zones around the colonies indicates lipase activity.

Subcloning and Restriction Site Mapping of Putative Fragment Containing Lipase Gene Recombinant plasmids from putative colonies were propagated and extracted according Qiaprep mini spin column (Qiagen) as mentioned earlier. The size of the insert was determined by digesting with BamH1 with the following reaction mixture setup of 10 µl [DNA (8 µl), restriction enzyme (1 µl), 10× RE buffer (1 µl)]. The reaction mixture was electrophoresed on 1% agarose gel (w/v) with 1 kb DNA ladder as marker. and then viewed under UV after staining for 20 minutes in ethidium bromide (1 mg/ml). After the size of the insert was determined, the insert was partially digested with Sau3A1 and subcloned into pUC 19 which was initially digested with BamH1 and dephosphorylized using calf intestinal alkaline phosphatase (CIAP). Recombinant clone was further rescreened with LB tributyrin-amp agar and LB triolein-amp agar. Double digestions of the pRSET/PI12lipase revealed a gene fragment of ~1.7 kb with BamH1 and Pst1 cutting sites flanking at both ends (FIG. 10). The ends of the insert were initially sequenced and the subsequent primers were designed to accomplish the sequence.

Sequencing and Analysis of the Cold Active Lipase Gene

The DNA was sent for automated DNA sequencing (Department of Biochemistry and Microbiology, UPM, Malaysia). Samples were sequenced using an ABI PRISM 377 Genetic Analyzer (Perkin-Elmer). Analysis of the sequence and database similarity research was done using the National Centre of Biotechnology (NCBI). Analysis of the lipase gene was done using Biology Workbench (www.biology.ncsa.sd-sc.edu) and Expasy Molecular Biology Server (www.expacy.org/tools). Vector pRSET (pRSET/PI12lipase) was designed to include T7 promoter and terminator regions for easy sequencing of an unknown insert of interests. Therefore, primers would encode this set if they were synthesized to sequence parts of the gene, in particular to the BamH1 (T7 promoter as the forward primer) and Pst1 sites (T7 terminator as the reverse primer).

Open Reading Frame (ORF) Predictions

The plasmid named pLipPI12 was used as a template for sequencing the insert. A sequence with the size of 1509 bp was obtained. The gene was analyzed for any possible open reading frames (ORFs) using the software called the ORF finder from the NCBI. One putative ORF was predicted with the size of 783 bp (denoted as LipPI12 gene), as shown in FIG. 11. The BLAST result revealed that LipPI12 showed a little homology with a lipase gene from *Pseudomonas* sp. UB140 (20% identity). This has been an agreement since other lipase genes from Gram negative bacteria, including *Pseudomonas* sp., were notably indicated to have quite a small ORF ranging from 800-1000 bp. Such functional lipase genes with small ORF were reported.

Expression of the Cold Adapted Lipase Gene

Primer Design

Primers were design to amplify the open reading frame which expressed the cold adapted lipase gene (LipPI12). The amplified products were cloned in frame with lac promoter in the pTrchis 2 TOPO TA in order to regulate the expression of the lipase gene with IPTG.

Construction of Cold Adapted Lipase Plasmid

Expression of cold adapted lipase gene in *E. coli* Top10 as the host was developed by using the pTrcHis2 TOPO (Invitrogen) expression system. The His tagged fusion system provides an integrated system for the expression and purification of the recombinant cold active lipase. This vector was design for Isopropyl-1-β-D-Galactopyranoside (IPTG) inducible expression of the recombinant lipase and engineered with an internal Lac z gene. Full length of the psychrophilic lipase gene (LipPI12) was prepared.

Expression of Cold Adapted Recombinant Lipase in *E. coli*

A culture derived from a colony harboring cold adapted lipase gene (*E. coli* Top10/pTrchis TOPO) was cultured in LB media containing 50 mg/L ampicillin salt. 200 ml of LB media were inoculated with transformed cells and empty vector and were incubated at 37° C. with shaking rates at 150 rpm. 1 mM of IPTG was added at a culture $A_{600}$ of 0.5-0.7. Bacterial growth and induction of the expressed protein and empty vector were continued and withdrawn hourly from 0-28 hours at 37° C. to check the optimum expression. Cell growth was measured spectrophotometrically at O.D 600 nm.

Intracellular Recombinant Lipase Extraction

The supernatant of the culture was prepared by removing the cells in the culture by centrifuging 10 ml of the culture at 12000×g for 10 minutes at 4° C. Before centrifuged, 1 ml of sample was taken for SDS-PAGE analysis in a discontinuous buffer system. After electrophoresis, gels were stained with Coomassie Brilliant Blue R-250 (0.5% w/v) in 25% (v/v) isopropanol and 10% (v/v) acetic acid for 30 minutes at room temperature with gentle agitation and distained with a mixture of methanol (10% v/v) and acetic acid (10% v/v) for 1 hour. The pelleted cells were resuspended in 10 ml of 20 mM phosphate buffer pH 7 and disrupted by sonication using an ultrasonic disruptor UD-200 at 60 W for 2 minutes with an interval of 30 s for every 1 minute of sonication in an ice bath. Cell extract was obtained by centrifugation at 12000×g and 4° C. for 10 minutes.

Extracellular Expression of Recombinant Cold Active Lipase

The BRP expression vector pJL3 was co-transformed into *E. coli* TOP 10 strain with the LipPI12 expression vector recombinant pBAD TOPO TA by using standard calcium chloride transformation procedures (Sambrook et al., 1989) in two steps process. The transformants were selected on LB plates containing chloramphenicol (35 µg/ml) and ampicillin (50 µg/ml) for pJL3/pBAD transformants. *E. coli* TOP 10 cells harbouring the expression plasmid were grown in 10 ml LB medium containing chloramphenicol (35 µg/ml) and ampicillin (50 µg/ml) overnight at 37° C. and subcultured in 100 ml LB medium containing chloramphenicol (34 µg/ml) and ampicillin (50 µg/ml) to grow to optical density of 0.5-0.6 at 600 nm for further investigation.

Intracellular Expression of Cold Adapted LipPI12

LipPI12 has been theoretically and computationally predicted, and was indicated as holding the prospect of being a cold active lipase. The expression of the lipase gene was done to assess its catalytic functions. Nonetheless, the expression of cold adapted proteins was a major task due to its thermolability and structural stability. The formation of inclusion bodies was something inevitable due to the very limited expression vector and its suitable host. Therefore, to cater for structure and function of the lipase structure, the expression was carried out at various temperatures of 25, 20 and 15° C. *E. coli* Top10 carrying pTrcHis2/LipPI12 was initially grown at 37° C. prior to induction. The cell culture was then induced with different concentrations of IPTG, ranging from 0 to 1 mM, and transferred to a lower temperature for further incubation. Primarily, the expression was performed at 25° C. with 1 mM of IPTG and was induced for 24 hours. Meanwhile, the lipase assay was done at 4° C. to screen the presence of cold active lipase activity. The lipase activity was detected at 0.1 U/ml.

As shown in FIG. 12, the crude lipase activity shows some effects of deterioration when exposed at higher temperature and vice versa. These findings may explain the thermolability of the protein. As the temperature increased, the recombinant LipPI12 may have undergone some structural changes which lead to altered folding and consequently increase inactive population (Feller et al., 1998). This indicates a glimpse of cold active enzyme characteristics. The activity was obviously and drastically decreased when tested at 40° C. Lower temperature seems to have good effect, with the optimum temperature at 20° C. The lipase exhibited an optimal activity of 0.15 U/ml. Therefore, LipPI12 gene is possible to be expressed at the lowest possible temperature, which is now optimally at 20° C. The work on LipPI112 gene expression was carried out at the stated temperature.

Optimization of Intracellular Expression of Cold Adapted LipPI12

Effect of Different Concentrations of IPTG on Secretory Expression of Cold Active Lipase Effect of different concentrations of inducer (IPTG) was studied by inducing the *E. coli* Top 10 harbouring recombinant plasmids pBAD and the BRP plasmid (pJL3) with different concentration of IPTG; 0 µM, 10 µM, 20 µM, 30 µM and 40 µM at OD600 nm ~0.5 for 4 h of induction time. The optimization of different concentrations of inducer (IPTG) was carried out. The protein expression level of recombinant *E. coli* was analyzed using sodium dodecyl sulphate-polyacrylamide gel electrophoresis (SDS-PAGE), as illustrated in FIG. 13. The results exhibited that the optimum concentration of IPTG was 0.3 mM, as the optimal activity exhibited in FIG. 14. In contrast, no recombinant enzyme activity was detected at a higher concentration of IPTG. This might probably be due the nature of the cold active enzyme itself. Unsuitable temperature, coupled with the enzyme unnatural host, could lead to psychrophilic enzyme improper folding. At a higher concentration of inducer and a lower temperature expression, the biological machinery is under stress, causing it to turn *E. coli* to be inefficient in expressing heterologous protein. The size was predicted to be around 27 kDa and its concomitant 6His tags (SEQ ID NO: 5) were around 3 to 4 kDa, giving a rise to an approximately 30 kDa protein. Therefore, as judged by the SDS PAGE (FIG. 14), the predicted molecular weight was almost the same. In terms of the lipolytic activity, the expression level was measured using the assay of lipase activity as suggested by Kwon and Rhea (1986) and for this, the lipase activity was found to be 0.25 U/ml.

Effect of Lipase Expression at Different Incubation Times

To study the optimum post induction time for the intracellular expression of pTrcHis2/LipPI12 lipase gene, different post induction times (0, 4, 8, 16, 24, 32 and 40 h) were tested and for these, 0.3 mM of IPTG was used as the optimum concentration of induction. The cells were grown primarily at 37° C. and transferred to 20° C. Indeed, the results showed that 32 hours of post induction time was the optimum with the lipase activity of 0.91 U/ml (FIG. 15). The induction expression profile, for both soluble and insoluble fractions, was observed using the SDS-PAGE, as depicted in FIG. 16. Besides the optimum concentration of the inducer as a reason, another reason for the optimum LipPI112 activity at 32 h of post induction time was the optimum growth of *E. coli*.

Secretory Expression of the Cold Adapted LipPI12 Gene

Co-expression of Bacteriocin Release Proteins (BRPs) facilitates secretory production of heterologous proteins from the cytoplasm of *E. coli*. BRP is a 28-amino-acid lipoprotein that activates detergent-resistant phospholipase A, resulting in the formation of permeable zones in the cell envelope through which proteins can pass into the culture medium (Lin et al., 2001; Fu et al., 2003). Extracellular production does not require outer-membrane disruption to recover target proteins, and, therefore, it avoids intracellular proteolysis by periplasmic proteases and allows continuous production of recombinant proteins. Based on these advantages, this strategy was done for the secretory expression of recombinant cold active LipPI12 lipase in *E. coli*.

Optimization of Extracellular Expression

In an attempt to obtain a higher level of lipase expression, the Bacteriocin Release Protein (BRP) expression vector pJL3 was co-transformed into *E. coli* TOP 10 strain, with the LipPI12 gene and the pBAD TOPO TA expression vector for the extracellular expression. This co-transformation enabled the acquisition of positive clones, which expressed LipPI12 and released it into the medium of the culture. Both Isopropyl-1-thio-D-galactopyranoside (IPTG) and L-arabinose were used for the induction of BRP and pBAD/LipPI12, respectively. The effect of different concentrations of inducer of Isopropyl-1-thio-D-galactopyranoside (IPTG), to induce the BRP plasmid (pJL3), were tested. The concentrations of IPTG used were 0 µM, 20 µM, 40 µM, and 60 µM at $OD_{600nm}$ ~0.5 for 24 h of induction time. The best (IPTG) concentration was 20 µM, while the extra-cellular lipase activity was 0.48 U/ml (FIG. 17). As a result, the over-expression of the BRP was proven to impose a negative effect to *E. coli*, whereby the intracellular and extracellular were found to be depleted at higher concentrations of 40 and 60 µM. The high-level expression of BRPs causes quasi-lysis and lethality.

As for the induction of the pBAD vector containing LipPI12 gene, different L-arabinose concentrations were experimented. Among the concentrations of 0%, 0.002%, 0.02% and 0.2% (w/v) L-arabinose, the optimal concentration was found to be at 0.002%, with extra-cellular lipase activity at 0.28 U/ml (FIG. 18). The increased activity, as compared with the intracellular expression, has revealed that the BRP system is an efficient way of producing heterologous protein and conducive for the heat labile protein from psychrophile. Cold active LipPI12 inclusion body formation has been reduced, and this has thereby promoted a better folding. As a matter of fact, the intracellular protein "congestion" had also been cleared as a result of bigger space provided in the medium of the culture.

Comparison Between Intracellularly and Extracellularly Expressed LipPI12

Approach of expressing LipPI12 gene intracellularly and extracellularly has is summarized. The best condition to express cold active LipPI12 gene intracellularly was achieved by using pTrchis 2 TOPO as expression vector. The time needed to get highest expression level was at 32 h with inducer (IPTG) concentration of 0.3 mM. As compared to extracellularly expressed LipPI12, different expression vector was used which was pBAD TOPO. Co-transformation of pJL3 plasmid which facilitate extracellular expression has yielded higher level of expression as expected. But still, the expression level shown to be lower than intracellularly expressed LipPI12. Plus the usage BRP protein has illustrated some minor drawback as it is lethal to *E. coli* when BRP is overexpressed. As a result cold active LipPI12 gene which was successfully expressed intracellularly will used for further investigation.

Protein Determination

The protein content was determined by the Bradford (1976) method using the Bovine serum albumin (BSA) as the standard.

SDS-PAGE Analysis of Bacterial Protein

Sodium dodecyl sulphate-polyacrylamide gel electrophoresis (SDS-PAGE) was prepared according to the method of Laemmli (1970). One ml of cells was taken out from induced culture medium and pelleted by centrifugation at 10 000 g and resuspended with 100 μl of phosphate buffer (pH 7.0). 100 μl of 2× sample buffer [15 ml 10% (w/v) SDS, 5% (v/v) glycerol, 2.5% (v/v) 2-mercaptoethanol. 6.25% (v/v) Upper buffer, 0.005% (w/v) bromophenol blue] and boiled for 10 min. Electrophoresis was carried out in Tris-glycine buffer [3% (w/v) Tris, 14.4% (w/v) glycine, 0.1% (w/v) SDS; pH 8.4] at a constant current of 30-35 mA for 90 min. After electrophoresis, gels were stained with Coomasie Brilliant Blue R-250 [0.5% (w/v) in 25% (v/v) isopropanol and 10% (v/v) acetic acid] for 30 min with gentle agitation in room temperature. The gels were later destained with destaining solution containing methanol [10% (v/v)] and acetic acid [10% (v/v)] for 1 h. Silver stained gels was done by using SilverXpress silver staining kit from Invitrogen according to manufacturer protocols.

Prediction of LipPI12 3D Structure

The PSI-BLAST at National Center for Biotechnology Information (www.ncbi.nlm.nih.gov/BLAST) was conducted to search for a suitable crystal structure in the database as a template. The 3D structure of PI12 mature lipase was predicted by homology modeling. The PI12 mature lipase sequence was modelled onto the crystal structure of the closest similarity using DS modeling software through align 2D, build model from MODELLER. Simple minimization (50 steps steepest descent and then 950 steps conjugate gradient) was performed in a water shell by AMBER with some restraints to good geometry regions. The final model was evaluated using Ramachandran plot.

Purification of Enzyme

The His tagged recombinant cold adapted lipase was purified using Nickel Sepharose affinity chromatography. The cells pellet was resuspended using 20 mM sodium phosphate (pH 7.4) binding buffer containing 20 mM imidazole and 0.5M NaCl. The sonicated cells were centrifuged at 120000×g for 30 minutes to separate the crude extract.

The crude enzyme was filtered and subjected to the affinity column that was preequilibrated with binding buffer. LipPI12 was eluted using elution buffer (pH 7.4) of 20 mM sodium phosphate containing 0.5M imidazole and 0.5M NaCl. The active fractions were pooled together and protein homogeneity was determined using SDS PAGE.

Purification of Recombinant Intracellularly and Extracellularly Expressed LipPI12

Protein purification from the recombinant strain has been made easier with the advancement of today's biotechnology. In addition to this, protein tags such as 6× Histidine (SEQ ID NO: 5), Gluthathione-S-Transferase, maltose binding protein and the like, have also been widely used. The addition of the tags reduces protein purification steps and therefore increases the yields and recovery. To facilitate the purification of protein, the recombinant cold adapted LipPI12 was tagged with the 6His residues (SEQ ID NO: 5). The Ni Sepharose Affinity chromatography method was applied, whereby the nickel ions inside the column possessed high affinity to the histidine residues. Chelating action took place and LipPI12 was eluted using a high concentration of imidazole, where it was responsible to replace the LipPI12 containing 6Histidine residues (SEQ ID NO: 5).

For the intracellularly expressed LipPI12, a single peak was obtained as shown in FIG. 19. The protein was successfully purified to homogeneity with the size of ~30 kDa as can be judged from the SDS PAGE and native PAGE exhibited in FIG. 20. The size of the protein corresponded well with the size predicted from the homology modelling, which was around 27 kDa plus 3 kDa of His tag. Since these psychrophilic proteins were largely expressed as insoluble forms, the reduction of incubation temperature during the expression had resulted in a considerable amount of soluble fractions. The inability for the enzyme to fold properly has become a major obstacle in protein purification; therefore purifying proteins from inclusion bodies is a daunting task and often results in a low recovery due to denaturation and increased purification steps. The intracellular LipPI12 was purified using only one step with a high recovery up to 75%, and specific activity folds to 42 (Table 3).

TABLE 3

Purification table of the intracellularly expressed recombinant cold adapted LipPI12

| Purification Step | Total Activity (U) | Total Protein (mg) | Specific Activity (U/mg) | Recovery (%) | Fold |
|---|---|---|---|---|---|
| Crude | 6 | 5.72 | 1.05 | 100 | 1 |
| Affinity Chromatography | 4.5 | 0.102 | 44.12 | 75 | 42 |

The extracellularly expressed recombinant LipPI12 was also successfully purified using the affinity chromatography. A single peak was successfully obtained in the elution profile as shown in FIG. 21 with 82% recovery and also increased purification fold of 8.17 (Table 4), which was much lower than the intracellular LipPI12. This was due to the concentration of protein from the starting sample where intracellular proteins were greatly higher as compared to the extracellular proteins. Therefore the purification fold tended to be lower.

TABLE 4

Purification table of the extracellularly expressed recombinant cold adapted LipPI12

| Purification Step | Total Activity (U) | Total Protein (mg) | Specific Activity (U/mg) | Recovery (%) | Fold |
|---|---|---|---|---|---|
| Crude | 3 | 0.935 | 3.21 | 100 | 1 |
| Affinity Chromatography | 2.464 | 0.094 | 26.21 | 82 | 8.17 |

The estimated size was also around 30 kDa as illustrated in FIG. 22. Both the expression and purification of the extracellularly expressed recombinant psychrophilic enzymes have not been reported. The success of LipPI12 is likely to be the first psychrophilic enzymes secreted outside the prokaryotic host which has successfully been purified to homogeneity.

Characterization of LipPI12 Lipase and Protease

Effect of Temperature on LipPI12 Lipase and Protease Activities

The effect of temperature on the purified LipPI12 was measured at temperatures ranging from 5 to 40° C. at 5° C. intervals for 30 min. It was assayed colorimetrically at a shaking rate of 200 rpm with olive oil and azocasein as substrates for lipase and protease respectively.

Molecular Modelling of Cold Adapted LipPI12

LipPI12 was a relatively small lipase compared to other bacterial lipases. LipPI12 consists of 783 amino acids encoding a protein of 27 kDa. The attempts to visualize and understand the functions of cold adapted LipPI12 were done using the homology modelling. The crystal structure of the psychrophilic protease from *Pseudomonas* sp. TACII18 (Ravaud et al., 2003) was chosen as a template since the closest homology is high, which was at 60% similarity. The similarity to protease was a striking evidence of how life has evolved at the cold environment and this has triggered the effort for deeper investigation. The flexibility of the protein may somehow lead to structural changes and eventually emerge an enzyme with additional properties. Surprisingly, enzymes from psychrophiles with multisubstrate properties have not been reported. As shown in FIG. 23, there is a distinctive beta roll, located at the centre of the enzyme structure. This may indicate $Ca^{2+}$ binding sites in accordance to its template, the psychrophilic protease TACII18 that comes to an agreement that lipases do possess the properties (Alquati et al., 2002). Other interesting features of the cold adapted LipPI12 are the extended loops and less compact structure, which give conformational freedom and increase the structural flexibility and activity at low temperature.

Model Evaluation

Model verification is essential in determining the correctness and accuracy of the LipPI12 3D model. Ramachandran plot is a useful way of achieving this purpose where it confers the overall stereo-chemical quality of the protein structure. RAMPAGE is one of the online tools (www.cryst.biochem.ac.uk/rampage) developed by Lovell et al. (2002); the tool can provide such information via the Ramachandran plot analysis.

Effect of Temperature on Stabilities of LipPI12 Lipase and Protease

Enzyme stability test was conducted by pre-incubating the LipPI12 at near optimum temperatures at 15 minute intervals for 2 hours prior to lipase and protease assays under shaking condition (200 rpm) for 30 min. As shown in FIG. 24, both the recombinant lipase and protease activities of LipPI12, at elevated temperatures, were drastically decreased. This was due to its high sensitivity to the heat or thermolability and as a consequence of its flexible structure Effect of pH on LipPI12 Lipase and Protease Activities The effect of pH the cold active lipase and protease activities was measured at various pHs (pH 4-12) under agitation rate of 200 rpm for 30 min. The buffer system involved various 50 mM acetate buffer (pH 4-6), potassium phosphate buffer (pH 6-8), Tris-Cl buffer (pH 8-9), glycine-NaOH (pH 9-11), and $Na_2HPO_3$/NaOH buffer (pH 11-12). The purified recombinant lipase was found to have an optimum pH at 7.0, indicating that LipPI12 was a neutral lipase (FIG. 25). On the other hand, protease was indicated to work best at a slightly higher pH, which is at pH 8 (FIG. 26). Nonetheless, both the enzymes generally work at the neutral condition. The decline of activities was observed in both lipase and protease in both acidic and basidic conditions. The pH of a solution can have several effects of the structural as well as the activity of the enzyme. Changing the pH will change the ionization of the amino acid chains and subsequently change the functionality of the enzyme. It is believed that there is a correlation between the pH and pK values of the amino acid chain. For instance, if an amino side chain like Lys is involved in a catalysis, it will probably only work when it is ionized. Therefore, at pH value below the pK of the Lys amino acid chain, which is about pH 9.0, the enzyme is active, while at the pH values above the Lys side chain pK, the enzyme becomes less active. In the end, the pH optimum lies somewhere between the pK values for these two groups, acidic and carboxylic side chain amino acid, which control the activity of the enzyme. The optimum pH of both lipase and protease LipPI12 is at the neutral pH value (pH7.0-8.0), which may probably be due to the abundancies of glycine throughout the structure, particularly in the active site.

Effect of Metal Ions on LipPI12 Lipase and Protease Activities

Various metal ions were tested by treating the purified enzyme with 1 mM of metal ions such as $Na^+$, $Mg^{2+}$, $Ca^{2+}$, $Fe^{2+}$, $Mn^{2+}$, $K^+$, $Zn^{2+}$ and $Cu^{2+}$ for 30 min at 20° C. It was subjected to lipase and protease assays after treatment. The effects of various metal ions were tested on the purified LipPI12 activity and the remaining activity was assayed using olive oil emulsion. $CaCl_2$ has increased the cold lipase LipPI12 activity to 115% as compared to the control. This is an indication which explains the role of Ca ion which may work as a stabilizer to the molecule, as predicted in the LipPI12 3D model. Whereas, the beta roll motif, served as a metal binding site, presumably predicted for the Ca ions. Interestingly, several monovalent and divalent metal ions showed a deteriorating effect on the lipase activity. $Na^+$ $Mg^{2+}$ and $Fe^{2+}$ have toxic effect to the enzyme. Other metal ions tested were $CuCl_2$, $ZnCl_2$ and $MnCl_2$, which had obviously made the lipase to be slightly stable and with no elimination of activity relatively not less than 50% (FIG. 27).

Protease LipPI12 looks more susceptible to all metal ions tested. In contrast to lipase, all metal ions did not negatively affect the proteolytic activity, but these exclude $Cu^{2+}$ and $Mn^{2+}$ with relative activity of 4 and 40%, respectively. Notably, several divalent metal ions were found to provide some effects on the catalytic performance of the protease LipPI12. Zn ion was found to increase its activity to 170% as compared to the control; while Ca, Mg, and Fe ions showed a stabilizing profile with a relative activity near or more than 100%. The incubation with $Na^+$ and IC ions had done little effect as compared to the destabilizing manner shown by divalent ions of $Cu^{2+}$ and $Mn^{2+}$. Surprisingly, LipPI12 did not show any similar conserved residue with respect to the metzincins clan, and only some portions of molecule are similar, which is the Ca binding site. A novel binding site for Zn ion may be involved in protease LipPI12. Structural elucidation is the best way to decipher the findings. The activation effect of Ca ion in both lipase and protease of LipPI12 is caused by the nature of the psychrophilic enzyme. Huge conformational movement will probably allow active residue rearrangement and can provide better accessibility of substrate, thus giving rise to a unique enzyme like LipPI12. This is achieved via local flexibility and mobility as the enzyme from psychrophiles evolves to withstand the extreme conditions, not only the coldness but also the low water content and substrate availability. Metal ions have been recognized to have effects on the activity of various enzymes. They bind the substrate and orient them properly for the reaction to occur. Besides mediating oxidation-reduction reactions, they can also electrostatically stabilize or shield negative charges. On the other hand, based on the correlation between the enzymes and metal ions, these enzymes could be classified into two types:

Metalloenzymes and Metal-activated enzyme. In Metalloenzyme, metal ions such as Fe, Cu, Mn, Co are tightly bound ion pairs. While in the metal-activated enzymes, the metal ions such as Na, K, Mg, and Ca are loosely bound metal ions from the solution. Based on these facts, the protease LipPI12 is considered as a metal-activated enzyme. Since metal ions such as $CuCl_2$, $ZnSO_4$ and $FeCl_3$ do not affect the LipPI12 activity, they are therefore confirmed as not utilizing metal ion to perform catalysis.

Effect of Surfactant on LipPI12 Lipase and Protease Activities

Surfactants or surface active agents are the most important constituents in the formulation of detergent. Enzyme and surfactants form unique interactions that affect the function of enzyme, i.e. whether to stabilize or destabilize. Enzymes especially lipases exhibit interfacial activation and can provide good effects via surfactant interactions. Lipase and protease LipPI12 was treated with various surfactants at a concentration of 1 mM at 20° C. for 30 min before being subjected to lipase and protease assays colorimetrically. The study on the effect of LipPI12 lipase and its protease on various surfactants was carried out using 0.1% of surfactant, namely from TWEEN™ 20-80, TRITON™ X-100, SDS and SLS. As shown in FIG. 34, LipPI12 tolerates in almost all surfactants tested but these exclude TWEEN™ 20. Remarkably, LipPI12 protease was activated in the presence of TWEEN™ 80 and SLS, with 30 and 70% enhancement, respectively. LipPI12 was also found to retain its activity when tested with TWEEN™ 40, 60 and TRITON™ X-100, as compared to the total inhibition effect of TWEEN™ 20. The incubation with SDS also seemed to affect LipPI12 protease catalytic activity, where it dropped to only 27% of its control activity.

Effect of Substrate Specificity on LipPI12 Lipase

Various triglycerides (triacetin, tributyrin, tricaprylin, triolein) p-nitrophenol esters (p-nitrophenylbutyrate, p-nitrophenylcaprylate, p-nitrophenyllaurate, p-nitrophenylpalmitate) and natural oils (olive oil, soy bean oil, corn oil, sun flower oil, rice brain oil, coconut and palm oil) were tested for the cold active LipPI12 lipase activity. It was assayed at 20° C. for 30 min colorimetrically. The capability of the LipPI12 to hydrolyze different carbon chain lengths of triglycerides was investigated. As shown in FIG. 28, LipPI12 could hydrolyze different carbon chain lengths of triglycerides between C4-C18, with an optimal activity within the medium length chain substrate, trilaurin (C12), and a relative activity of 100% was obtained. Nevertheless, the lipase poorly exhibited hydrolysis of the short chain substrates C4-C8, and the same phenomenon was also observed with the long chain substrate. LipPI12 lipase substrate specificity towards medium chain length was also observed in natural oils. As shown in FIG. 29, LipPI12 has the highest preference to coconut oil, with majority of fatty acids component contains C12 which records more than 200% of the relative activity as compared to other natural oils being tested. Non-specificity towards other substrate containing C16-C18 was shown to reduce the activity which entailed similar findings as experimented using pure triglycerides. Interestingly, when tested using natural oils, containing unsaturated fatty acid (C18:2), LipPI12 showed lower relative activity as found in sunflower, corn and soybean oils with the relative activity recorded lower than 50%. LipPI12 low efficiency or inability to catalyze such substrate was probably due to improper substrate and active coordination and limited substrate accessibility as a result of cis conformation of aliphatic chain when compared to the trans conformation which is much linear. Artificial substrate was also used in the form of esters, namely para-nitrophenyl (pNP) esters containing carbon chain ranging from C4 (butyrate) to C16 (palmitate). The hydrolyzing effect of LipPI12 on these pNP esters exhibited a slightly different pattern as compared to using triglycerides and natural oils (FIG. 30). This seems to suggest that pNP palmitate (C16) serves as a better substrate, with 60% increment of activity in relative to other pNP esters including butyrate (C4), caprylate (C8) and laurate (12). Certainly, LipPI12 broad substrate specificity, which posed a huge prospect in application and the understanding of mechanism, is important. Nonetheless, the profile of substrate is a crucial point, where accessibility determines substrate specificity. This in turn reflects LipPI12 unique properties especially active site adaptation is a facile explanation. The capability of LipPI12 to hydrolyze carbon chain lengths of triglycerides in the medium length chain range indicated that the lipase was true lipase and not esterase; since the latter is unable to hydrolyze carbon chains of more than C4. As a matter of fact, there is no particular trend for lipases in their hydrolysis of different carbon chain lengths of triglycerides as substrates because different lipases only act in accordance to their own behaviours.

Effect of Inhibitors on LipPI12 Lipase and Protease Activities

Partial understanding of the enzyme catalysis involves the reaction with various inhibitors. Although it provides indirect information, it also gives a better view via the reaction on specific inhibitors to its specific ligands. These include the usage of the inhibitors such as the EDTA (ethylene diamine tetraacetic acid) a metalloenzyme inhibitor, PMSF (phenylmethylsulphonyl fluoride) a serine protease inhibitor and Pepstatin, which works best on enzyme utilizing aspartate as one of its catalytic residues. Various inhibitors were tested at a final concentration of 1 mM (PMSF, EDTA and pepstatin). The purified enzyme was treated with various inhibitors at 20° C. for 30 min prior to measuring the residual activity colorimetrically. Interestingly, LipPI12 dual activities might be working well at a different active site or utilizing the same active cavity as shown in FIG. 35, but with different involvements of catalytic residues. At the inhibitors strength of 1 mM, the protease activity was drastically eliminated. This showed that the aspartate be involved in the LipPI12 proteolytic property. EDTA and PMSF, on the other hand, gave quite a substantial inhibition after more that 50% of the protease activity had been reduced. The effect of the PMSF has showed that serine does play a part in the enzyme activity and with the aspartate showing higher degree of inhibition, a catalytic dyad or triad.

Solvent Tolerant Profile of LipPI12 Lipase and Protease

Study On LipPI12 organic solvent stability was carried out in reaction mixture containing purified LipPI12 and various solvents. The mixture was incubated at 20° C. with shaking rates at 150 rpm for 30 min. Control reaction was done by mixing the enzyme with water. Relative activity of lipase was determined according Kwon and Rhee (1986) method. Whereby protease assay was done according to Brock et, al., (1982). The effects of various organic solvents on the stability of the cold active LipPI12 were studied. A mixture of 3 ml enzyme solution and 1 ml of an organic solvent was incubated at 20° C. with shaking, and the remaining activity was measured after 30 min of incubation. As shown in FIG. 31, the lipase was found to have a good stability in the presence of hexadecane, benzene, dodecane and heptane, with dimethylsulfonyl being the most stabilizing (~80% increase of activity). However, the lipase exhibited a decrease in more than 50% of its activity in the presence of toluene. Meanwhile, the reaction of lipase LipPI12 in propanol was shown to have a significant increase in activity with value over than 160%.

Diethyleter, hexane, decane and heptane were proven to be the most destructive solvents for LipPI12, based on the total elimination of activity. Surprisingly for its protease counterpart, most of the LipPI12 activities were enhanced in the presence of hydrophilic solvents ($-1.22<\log P_{o/w}<0$), even though the enzymes were generally inactivated by the solvents at this range of log $P_{o/w}$. In contrast to lipase, the protease exhibited tolerance, towards organic solvents of high hydrophilicity and hydrophobicity, such as the dimethylsulphonyl and hexadecane, respectively. Nevertheless, some LipPI12 activities were observed to be destabilized by water-immiscible organic solvents with log $P_{o/w}>4$, although the enzymes are little affected by these solvents. In fact, the protease also showed a significant resilient to benzene, dodecane and heptane, with the activity was still more than 100% as compared to the reaction in water. This led to the understanding that the protease is more tolerant than lipase. However, the different profiles were shown by both the enzymes of LipPI12, even though they existed as a single unit which might somehow elucidate a new adaptation in terms of their molecular architecture.

Themostability Profile of LipPI12 Lipase and Protease

The thermostability profile of LipPI12 was studied by pre-incubating the enzyme at 15 min intervals at near optimal temperature of the respective enzymes. The cold active lipase of LipPI12 was tested at 15 and 20° C. For these, the lipase recorded an optimal activity at 20° C. but the results showed that it was not thermostable when challenged at prolonged incubation up to 120 min (FIG. 32). The lipase lost its threshold half-life right after 30 mins. The same pattern of thermolability could also be observed at 15° C. This explained the cold active lipase psychrophilic properties. Temperature is a vital aspect in cold adaptation. Although the LipPI12 protease showed a higher optimal temperature (35° C.) as compared its twin partner, the themostability profile on the other hand, exhibited quite a similar story. The protease part was relatively deactivated when incubated at a prolonged incubation in the same temperature (FIG. 33). It resulted in a shorter half-life, not more than 15 mins of incubation, and would surely experience a total elimination of activity after more than 90 mins of incubation. The higher temperature exposure must have severely affected the overall conformation of LipPI12 protease. The high temperature caused the vibrational movement of the molecule to increase and the high energy released was unbearable to the weak and unstable conformation of LipPI12. This is where temperature can play its part and is a point of manipulation in low temperature industries. Enzyme easy deactivation is a useful method to control reaction.

Composition of Amino Acid and the Hydrophobicity Profile of LipPI12

LipPI12 protein sequence hydrophobicity profile was analysed using the Protscale tool which was derived from the Expasy Molecular Biology server. The programme was developed by Kyte and Doolittle (1982).

LipPI12 consists of 260 amino acids and these exclude the cystein residue. The absence of cystein may have probably made it more flexible because no disulphide bridge is formed. As shown in FIG. 36, there are two distinct domains of hydrophilic and hydrophobic, respectively. The first 100 amino acids are very much hydrophilic and may explain that they are present or protruded to the environment or to the cytosol in the wild type strain. In fact, this finding can provide further information about the location of the biological activity, i.e. whether the lipase or its protease counterpart is sharing the active site or vice versa. On the other hand, the second domain, which is more hydrophobic, had shown that it could serve as the protein anchor. This can also explain it as a membrane protein. However, the exact biological location of LipPI12 still remains unclear.

Comparison of Amino Acid

Different microorganism from extremophile family uses different type of adaptation in order to survive such harsh conditions. Microbial adaptation in general poses a unique story perhaps on its architecture and most of all of course coming from its enzyme. Enzyme from psychrophiles holds something that is still a mystery and has been understudied. Stability has been regarded as an important factor for enzyme to be active. But it is a different case for those coming from the cold.

The building block of cold active LipPI12 comprises 260 amino acids. Interestingly no cystein is the sequence. LipPI12 bears some signature from psychrophilic enzyme. Majority of the residues is glycine, resembling 13.5% of the LipPI12 total residues and proline; whereas a rigid amino acid was shown to be the lowest amount of residue with only 0.8%. The increment and reduction of glycine and proline will respectively favour more towards a flexible structure. Compared to its other counterparts, lesser amounts of glycine and more proline were observed as the temperature profile increased (Table 5). In terms of ratio, LipPI12 showed a lower ratio of glycine and proline, as compared to S5lipase (Baharum, 2005) and T1lipase (Leow et al., 2004). The consequence is LipPI12 becomes unstable, but conducive enough to be active via a flexible conformation.

TABLE 5

Comparison of amino acid composition (%) of cold active LipPI12 with thermophilic enzyme, T1lipase and mesophilic enzyme, S5lipase

| Amino acid | LipPI12 | S5Lipase | T1Lipase |
|---|---|---|---|
| Ala (A) | 13.1% | 10.0% | 7.9% |
| Arg (R) | 1.5% | 14.9% | 6.5% |
| Asn (N) | 5.8% | 4.3% | 4.6% |
| Asp (D) | 10.4% | 3.3% | 5.5% |
| Cys (C) | 0.0% | 3.3% | 1.0% |
| Gln (Q) | 4.2% | 3.3% | 3.1% |
| Glu (E) | 2.3% | 5.4% | 4.8% |
| Gly (G) | 13.5% | 8.9% | 10.1% |
| His (H) | 0.4% | 1.9% | 3.1% |
| Ile (I) | 5.4% | 3.0% | 3.1% |
| Leu (L) | 8.8% | 7.3% | 9.6% |
| Lys (K) | 3.8% | 3.5% | 2.9% |
| Met (M) | 0.4% | 0.8% | 1.9% |
| Phe (F) | 4.6% | 0.8% | 4.8% |
| Pro (P) | 0.8% | 6.2% | 4.6% |
| Ser (S) | 9.6% | 7.0% | 6.5% |
| Thr (T) | 4.6% | 4.1% | 6.0% |
| Trp (W) | 1.2% | 3.5% | 2.4% |
| Tyr (Y) | 3.5% | 2.7% | 4.6% |
| Val (V) | 6.2% | 5.7% | 7.0% |

Note:
The amino acid sequence was obtained from the Genbank. The accession numbers used are ABC70165 (LipPI12); AY787283 (S5lipase); AY260704 (T1lipase)

Biophysical Analysis of LipPI12

Circular Dichroism (CD) Spectra Analysis of LipPI12

The purified cold active LipPI12 in sodium phosphate buffer (pH 8.0) was analysed with spectropolarimeter J-810 (Jasco, Japan) for CD spectral analysis. The warm-up periods of 5 to 45° C. and wavelength scan of 180 to 250 nm were taken into consideration.

Denatured Protein Analysis

The variable temperature measurement of LipPI12 was performed by employing 2 mm cell after checking the CD value at 220 nm. The warm-up period was 5-45° C., and the step was 1 degree per minute. The wavelength was set to 220 nm. The concentration was 1 mg/mL and top of the cell was completely closed using a cap. Data pitch, bandwidth, response, scanning speed, and accumulation were set to be 0.1 degree, 1 nm, 8 seconds, 1 degree per minute, 8 times, respectively.

Polypeptide conformations, which determine protein secondary structures, give rise to circular dichroism spectra (Yang et al., 1986). CD measurements have been widely used to follow the equilibrium between helical structures and unordered conformations (Schröder et al., 2001). The CD spectra (molecular ellipticity) of LipPI12 was analysed as a function of temperature at 220 nm (FIG. 37). Meanwhile, the wavelength 220 nm was set to monitor the transition of α-helical to unordered structures, as they exhibited characteristic signals at this particular wavelength. The high tension voltage (HT) value gradually increased until the $T_m$ of LipPI12, and this was then decreased as LipPI12 was unfolded above the melting temperature point. This might be due to loss of the secondary structure of protein, followed by an increase in the unordered conformations. The sigmoidal shape of the resulting denaturation curve indicated a monophasic helix-coil transition of LipPI12 within the analysed temperature range. The fitting lines were extrapolated, from the stable region to the range of denaturation (24.0-53.7° C.), in order to obtain the $T_m$ value. As shown in FIG. 48, the $T_m$ value of LipPI12 for this transition was 38° C. According to the second law of thermodynamics, the free energy change (ΔG), at constant temperature and pressure, is ΔG=ΔH−TΔS (Brady et al., 2000). When a protein started to unfold due to heating, the process would go through an intermediate state, thus the free energy change (ΔG) at equilibrium was zero. As a consequence, the LipPI12 showed a melting temperature ($T_m$) of 38° C. as the unfolding enthalpy ΔH and entropy ΔS were −35.03 kcal/mol and −0.112 kcal/mol/K, respectively (Table 6). In agreement to these, the half-life for lipase LipPI12 was indicated to be around 20° C., as the treatment temperature was slightly below its $T_m$ of 38° C. The $T_m$ value of LipPI12 was still in the range of LipPI12 protease part, in which the protease activity was at 35° C. With the optimal activity recorded at 35° C., it was shown that the enzyme had suffered a conformational change which would further lead to denaturation.

TABLE 6

Thermodynamic profile in accordance to $T_m$, dH and dS

| Sample | Tm (° C.) | dH (kcal/mol) | dS |
|---|---|---|---|
| LipPI12 | 38.61 | −35.03 | −0.112 |

Fluorescence Spectrofluorometry

Intrinsic fluorescence was measured on a Shimadzu RF-5301 (Shimadzu, Japan). The excitation wavelength was set at 295 nm and the emission was scanned between 310 and 500 nm.

As for the extrinsic fluorescence which utilized 8-anilino-1-naphthalenesulfonic acid (ANS) as fluorescence probe, the ANS emission was scanned between 400 and 650 nm with an excitation wavelength of 350 nm. All the experiments were carried out with the protein concentrations of 25 μg/mL in 50 mM sodium phosphate buffer pH 8. The final concentration of ANS in the enzyme solutions was 50 μM. FIG. 38 shows the intrinsic fluorescence of the tryptophan residues derived from LipPI12 after being treated at various temperatures which ranged between 5-40° C. for 30 minutes. There was a significant emission enhancement when incubated at higher temperature with little peak shifting. This indicates or suggests that all the three tryptophan residues are well placed or exposed to the environment. Although it was not confirmed via crystal structure, it comes with an agreement from the predicted model (FIG. 39). As far as the predicted structure is concerned, all the indole ring of tryptophan was not located at the hydrophobic core of LipPI12. LipPI12 showed a similar emission of fluorescence intensity at every temperature tested (FIG. 40). This finding proves that the cold active LipPI12 holds a typical characteristic of a psychrophilic enzyme.

Characteristics of LipPI12 Lipase and Protease

| Protein Characteristic | Lipase | Protease |
|---|---|---|
| Molecular Wight (kDa) | | 27 (monomer) |
| Temperature optimum (° C.) | 20 | 40 |
| pH optimum | 7 | 8 |
| Metal ion | Ca | Ca, Mg, Zn |
| Surfactant | Tween Sodium lauryl sulphate 80 | Tween 20 |
| Organic solvent tolerance | | Dimethylsulfonyl, benzene, propanol, decane, hexadecane, dodecane |
| Inhibitor | PMSF | Pepstatin, EDTA |
| CD analysis (Tm) | | 38° C. |
| Fluorescence spectrum analysis | | Non compact structure, less hydrophobic core |

The invention claimed is:

1. An isolated bifunctional enzyme comprising a polypeptide set forth in SEQ ID NO:2, wherein the isolated bifunctional enzyme has a cold active lipase activity and a protease activity.

2. The isolated bifunctional enzyme of claim 1, wherein the cold active lipase activity occurs at a temperature between 4° C. and 35° C. and the protease activity occurs at a temperature between 4° C. and 45° C.

3. The isolated bifunctional enzyme of claim 1, wherein the polypeptide is encoded by the nucleotide sequence of SEQ ID NO:1.

4. The isolated bifunctional enzyme of claim 1, wherein the isolated bifunctional enzyme is obtained from *Leucosporodium antarcticum*.

5. The isolated bifunctional enzyme of claim 1, wherein the bifunctional enzyme includes one or more of the following characteristics:
   a) ability to function at a temperature range from 5° C. to 40° C. with an optimum temperature at least 20° C. for the cold active lipase activity and 35-40° C. for the protease activity;
   b) ability to function at a pH range of pH 4 to 12;
   c) ability to act on one or more substrates selected from the group consisting of triglycerides, p-nitrophenol esters and natural oils, wherein the triglycerides are triacetin, tributyrin, tricaprylin or triolein, wherein the p-nitrophenol esters are selected from the group consisting of p-nitrophenylbutyrate, p-nitrophenylcaprylate, p-nitrophenyllaurate, and p-nitrophenylpalmitate, and the natural oils are selected from the group consisting of olive oil, soy bean oil, corn oil, sun flower oil, rice bran oil and palm oil; or d) ability to be inhibited by phenylmethanesulfonylfluoride (PMSFL ethylenediaminetetraacetic acid (EDTAL or pepstatin.

6. The isolated bifunctional enzyme of claim 1, wherein the polypeptide is linked to a protein tag.

7. The isolated bifunctional enzyme of claim 1, wherein the protein tag is selected from the group consisting of a 6× Histidine tag, a Glutathione-S-transferase tag, and a maltose binding protein tag.

* * * * *